(12) United States Patent
Akao et al.

(10) Patent No.: US 11,771,140 B2
(45) Date of Patent: Oct. 3, 2023

(54) INHALATION COMPONENT GENERATION DEVICE, METHOD FOR CONTROLLING INHALATION COMPONENT GENERATION DEVICE, AND PROGRAM

(71) Applicant: JAPAN TOBACCO INC., Tokyo (JP)

(72) Inventors: Takeshi Akao, Tokyo (JP); Takuma Nakano, Tokyo (JP); Hajime Fujita, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 617 days.

(21) Appl. No.: 16/851,127

(22) Filed: Apr. 17, 2020

(65) Prior Publication Data
US 2020/0281277 A1    Sep. 10, 2020

Related U.S. Application Data

(63) Continuation of application No. PCT/JP2017/037754, filed on Oct. 18, 2017.

(51) Int. Cl.
*A24F 40/90* (2020.01)
*G01R 31/392* (2019.01)
*G01R 31/3842* (2019.01)
*A24F 40/53* (2020.01)
*A24F 40/51* (2020.01)
(Continued)

(52) U.S. Cl.
CPC ............ *A24F 40/90* (2020.01); *A24F 40/51* (2020.01); *A24F 40/53* (2020.01); *G01R 31/3842* (2019.01); *G01R 31/392* (2019.01); *H02J 7/0047* (2013.01); *A24F 40/10* (2020.01)

(58) Field of Classification Search
None
See application file for complete search history.

(56) References Cited

U.S. PATENT DOCUMENTS

| | | |
|---|---|---|
| 5,561,362 A | 10/1996 | Kawamura et al. |
| 6,236,215 B1 | 5/2001 | Kanehira |
| 2002/0053490 A1 | 5/2002 | Banno et al. |

(Continued)

FOREIGN PATENT DOCUMENTS

| | | |
|---|---|---|
| CN | 101228697 A | 7/2008 |
| CN | 103675685 A | 3/2014 |

(Continued)

OTHER PUBLICATIONS

Chinese Office Action dated Nov. 22, 2021, in corresponding Chinese Patent Application No. 201780096103.4.

(Continued)

*Primary Examiner* — Jas A Sanghera
(74) *Attorney, Agent, or Firm* — XSENSUS LLP

(57) ABSTRACT

An inhalation component generation device includes a load configured to vaporize or atomize an inhalation component source with electric power from a power supply, and a control unit configured to be capable of acquiring a value related to an operation amount of the load and a voltage value of the power supply. The control unit is configured to be capable of estimating or detecting at least one of degradation and failure of the power supply based on the value related to the operation amount of the load operated in a period in which the acquired voltage value of the power supply is in a predetermined voltage range.

18 Claims, 17 Drawing Sheets

(51) Int. Cl.
*H02J 7/00* (2006.01)
*A24F 40/10* (2020.01)

(56) References Cited

U.S. PATENT DOCUMENTS

| | | | |
|---|---|---|---|
| 2002/0196025 | A1 | 12/2002 | Freeman et al. |
| 2005/0212505 | A1 | 9/2005 | Murray et al. |
| 2009/0167575 | A1 | 7/2009 | Mitani et al. |
| 2011/0265806 | A1 | 11/2011 | Alarcon et al. |
| 2012/0158338 | A1 | 6/2012 | Yang et al. |
| 2012/0230659 | A1 | 9/2012 | Goodman et al. |
| 2013/0300425 | A1 | 11/2013 | Shiraishi et al. |
| 2013/0306084 | A1 | 11/2013 | Flick |
| 2014/0077818 | A1 | 3/2014 | He et al. |
| 2015/0036250 | A1 | 2/2015 | Xiang |
| 2015/0189916 | A1 | 7/2015 | Wu |
| 2015/0212161 | A1 | 7/2015 | Soga et al. |
| 2015/0374040 | A1* | 12/2015 | Chen ............... G01R 31/66 131/328 |
| 2016/0057811 | A1 | 2/2016 | Alarcon et al. |
| 2016/0213066 | A1 | 7/2016 | Zitzke et al. |
| 2016/0242466 | A1 | 8/2016 | Lord et al. |
| 2017/0027234 | A1 | 2/2017 | Farine et al. |
| 2017/0119052 | A1 | 5/2017 | Williams et al. |
| 2017/0238605 | A1 | 8/2017 | Matsumoto et al. |
| 2017/0238606 | A1 | 8/2017 | Matsumoto et al. |
| 2018/0226695 | A1 | 8/2018 | Miyaki et al. |
| 2019/0307166 | A1 | 10/2019 | Matsumoto et al. |

FOREIGN PATENT DOCUMENTS

| | | |
|---|---|---|
| CN | 205214209 U | 5/2016 |
| CN | 105764366 A | 7/2016 |
| EP | 2 701 268 A1 | 2/2014 |
| EP | 2856893 A1 | 4/2015 |
| EP | 3 219 212 A1 | 9/2017 |
| JP | 06-242192 A | 9/1994 |
| JP | 07-128416 A | 5/1995 |
| JP | 07-184627 A | 7/1995 |
| JP | 07-239735 A | 9/1995 |
| JP | 09-26470 A | 1/1997 |
| JP | 11-052033 A | 2/1999 |
| JP | 11-237455 A | 8/1999 |
| JP | 2000-251948 A | 9/2000 |
| JP | 2001-094661 A | 4/2001 |
| JP | 2002-34164 A | 1/2002 |
| JP | 2002-148323 A | 5/2002 |
| JP | 2003-100356 A | 4/2003 |
| JP | 2003-317811 A | 11/2003 |
| JP | 2005-538499 A | 12/2005 |
| JP | 2007-168305 A | 7/2007 |
| JP | 2007-180972 A | 7/2007 |
| JP | 2010-050045 A | 3/2010 |
| JP | 2010-122162 A | 6/2010 |
| JP | 2012-70474 A | 4/2012 |
| JP | 2014-501106 A | 1/2014 |
| JP | 2014-48101 A | 3/2014 |
| JP | 2014-512207 A | 5/2014 |
| JP | 2014-131872 A | 7/2014 |
| JP | 2016-176709 A | 10/2016 |
| JP | 2016-533712 A | 11/2016 |
| JP | 2017-005985 A | 1/2017 |
| JP | 2017-022852 A | 1/2017 |
| JP | 2017-514463 A | 6/2017 |
| JP | 6176383 B1 | 8/2017 |
| JP | 2017-167034 A | 9/2017 |
| WO | 2014/046232 A1 | 3/2014 |
| WO | 2014/150942 A2 | 9/2014 |
| WO | 2016/075747 A1 | 5/2016 |
| WO | 2016/076178 A1 | 5/2016 |
| WO | 2016075748 A1 | 5/2016 |
| WO | 2017/013823 A1 | 1/2017 |

OTHER PUBLICATIONS

Office Action dated Jul. 27, 2022, in corresponding Chinese patent Application No. 201780096112.3.
Office Action dated Jul. 26, 2022, in corresponding Chinese patent Application No. 201780096111.9.
International Search Report and Written Opinion dated Dec. 26, 2017 for PCT/JP2017/037754 filed on Oct. 18, 2017, 12 pages including English Translation of the International Search Report.
International Search Report and Written Opinion dated Dec. 26, 2017 for PCT/JP2017/037752 filed on Oct. 18, 2017, 9 pages including English Translation of the International Search Report.
International Search Report and Written Opinion dated Dec. 19, 2017 for PCT/JP2017/037755 filed on Oct. 18, 2017, 8 pages including English Translation of the International Search Report.
International Search Report and Written Opinion dated Jan. 23, 2018 for PCT/JP2017/03//56 filed on Oct. 18, 2017, 9 pages including English Translation of the International Search Report.
U.S. Office Action dated Dec. 20, 2021, in corresponding U.S. Appl. No. 16/851,135.
Notice of Reasons for Refusal dated Mar. 11, 2020 in Japanese Patent Application No. 2019-549055, 4 pages.
Decision to Grant a Patent dated Apr. 9, 2020 in Japanese Patent Application No. 2019-549055, 5 pages.
Office Action dated Oct. 28, 2021, in corresponding Korean patent Application No. 2020-7013246, 22 pages.
Extended European search report dated Oct. 2, 2020, in corresponding European patent Application No. 17928906.1, 8 pages.
Canadian Office Action dated Jun. 16, 2021, in corresponding Canadian Patent Application No. 3,079,154.
Extended European Search Report dated Oct. 13, 2020 in European Patent Application No. 17929079.6, 8 pages.
Extended European Search Report dated Oct. 16, 2020 in European Patent Application No. 17929222.2, 8 pages.
Extended European Search Report dated Oct. 16, 2020 in European Patent Application No. 17929279.2, 10 pages.
Office Action dated Jun. 5, 2020 in Japanese Patent Application No. 2019-549057, 5 pages.
Office Action dated Jun. 24, 2020 in Japanese Patent Application No. 2019-549056, 13 pages.
Office Action dated Jun. 29, 2020 in Japanese Patent Application No. 2019-549058, 12 pages.
Canadian Office Action issued May 25, 2021, in corresponding Canadian Patent Application No. 3,079,163.
U.S. Office Action dated Nov. 27, 2020 in co-pending U.S. Appl. No. 16/851,278, 53 pages.

* cited by examiner

INHALATION COMPONENT GENERATION DEVICE, METHOD FOR CONTROLLING INHALATION COMPONENT GENERATION DEVICE, AND PROGRAM

CROSS REFERENCE TO RELATED APPLICATIONS

The present application is a continuation application of International Application No. PCT/JP2017/037754, filed on Oct. 18, 2017.

TECHNICAL FIELD

The present invention relates to an inhalation component generation device including a load configured to vaporize or atomize an inhalation component source with electric power from a power supply, a method of controlling the inhalation component generation device, and a program.

BACKGROUND ART

Instead of a conventional cigarette, there has been proposed an inhalation component generation device (an electronic cigarette or heated tobacco) used for tasting an inhalation component generated by vaporizing or atomizing a flavor source such as tobacco or an aerosol source with a load such as a heater (PTL 1 to PTL 3). Such an inhalation component generation device includes a load configured to vaporize or atomize a flavor source and/or an aerosol source, a power supply configured to supply electric power to the load, and a control unit configured to control the load and the power supply. The load is, for example, a heater.

In such an inhalation component generation device, there is room for improvement in the electric control regarding the electric power to be supplied to the load and the charge and discharge of the power supply.

PTL 4 to PTL 6 each disclose a method of estimating the degree of degradation of a power supply. PTL 7 and PTL 8 each disclose a method of monitoring the abnormality of a power supply. PTL 9 discloses a method of suppressing the degradation of a power supply. PTL 10 to PTL 12 each disclose calibrating a state of charge (SOC) and charge capacitance of a battery when the power supply reaches a full charge under predetermined conditions. PTL 4 to PTL 12 each do not specify that the above-described methods are applied to the inhalation component generation device.

CITATION LIST

Patent Literature

PTL 1: International Publication No. WO 2014/150942
PTL 2: National Publication of International Patent Application No. 2017-514463
PTL 3: Japanese Patent Laid-Open No. 7-184627
PTL 4: Japanese Patent Laid-Open No. 2000-251948
PTL 5: Japanese Patent Laid-Open No. 2016-176709
PTL 6: Japanese Patent Laid-Open No. 11-052033
PTL 7: Japanese Patent Laid-Open No. 2003-317811
PTL 8: Japanese Patent Laid-Open No. 2010-050045
PTL 9: Japanese Patent Laid-Open No. 2017-005985
PTL 10: International Publication No. WO 2014/046232
PTL 11: Japanese Patent Laid-Open No. 7-128416
PTL 12: Japanese Patent Laid-Open No. 2017-022852

SUMMARY OF INVENTION

A first feature provides an inhalation component generation device including a load configured to vaporize or atomize an inhalation component source with electric power from a power supply, and a control unit configured to be capable of acquiring a value related to an operation amount of the load and a voltage value of the power supply, wherein the control unit is configured to be capable of estimating or detecting at least one of degradation and failure of the power supply based on the value related to the operation amount of the load operated in a period in which the acquired voltage value of the power supply is in a predetermined voltage range.

The second feature provides the inhalation component generation device according to the first feature, wherein the value related to the operation amount of the load is an amount of electric power supplied to the load, or an operation time, a temperature or the number of operations of the load.

The third feature provides the inhalation component generation device according to the first feature, wherein the value related to the operation amount of the load is a consumption amount of the inhalation component source.

The fourth feature provides the inhalation component generation device according to the first feature, further including a replaceable cartridge containing the inhalation component source, wherein the value related to the operation amount of the load is the number of replacement times of the cartridge.

The fifth feature provides the inhalation component generation device according to the first feature or the second feature, further including a sensor configured to be capable of outputting a signal requesting an operation of the load, wherein the control unit is configured to be capable of deriving the value related to the operation amount of the load based on an output of the sensor.

The sixth feature provides the inhalation component generation device according to the fifth feature, further including an inhalation port for inhaling by a user, wherein the sensor is configured to output an output value that varies depending on inhalation from the inhalation port, the control unit is configured to detect the inhalation according to the output values from the sensor, and the control unit is configured to be capable of deriving the value related to the operation amount of the load based on at least one of a detected inhalation period and inhalation amount.

The seventh feature provides the inhalation component generation device according to the sixth feature, wherein the output value is a value related to a pressure change in the inhalation component generation device, and the control unit is configured to detect the inhalation only when an absolute value of the output value is equal to or larger than a predetermined threshold.

The eighth feature provides the inhalation component generation device according to any one of the fifth feature to the seventh feature, wherein the control unit includes a power control unit configured to control a power supply from the power supply to the load, and the power control unit is configured to equalize the electric power to be supplied from the power supply to the load among a plurality of times of the inhalation or operations of the load.

The ninth feature provides the inhalation component generation device according to any one of the fifth feature to the eighth feature, wherein the control unit includes a power control unit configured to control a power supply from the power supply to the load, and when the control unit detects a request for the inhalation or operations of the load, the power control unit is configured to control a voltage to be applied to the load in a pulse width modulation having a duty ratio that increases as the voltage value of the power supply decreases.

The tenth feature provides the inhalation component generation device according to any one of the first feature to the ninth feature, wherein the control unit is configured to compare the value related to the operation amount of the load operated in a period in which the acquired voltage value of the power supply is in the predetermined voltage range with a predetermined threshold, and to determine that the power supply has been degraded or has failed when the value related to the operation amount of the load is equal to or less than the predetermined threshold.

The eleventh feature provides the inhalation component generation device according to the tenth feature, wherein the control unit is configured not to perform determination of degradation or failure of the power supply in the predetermined voltage range when a range contributing to vaporization or atomization of the inhalation component source in the predetermined voltage range is equal to or less than a predetermined ratio or width.

The twelfth feature provides the inhalation component generation device according to the tenth feature, wherein the control unit is configured to correct to reduce at least one of the predetermined threshold and a lower limit value of the predetermined voltage range when the range contributing to the vaporization or atomization of the inhalation component source in the predetermined voltage range is equal to or less than a predetermined ratio or width.

The thirteenth feature provides the inhalation component generation device according to any one of the tenth feature to the twelfth feature, wherein the control unit is configured to perform the comparison in each of the plurality of predetermined voltage ranges, and to determine that the power supply has been degraded or has failed when the value related to the operation amount of the load is equal to or less than the predetermined threshold in at least one of the plurality of predetermined voltage ranges.

The fourteenth feature provides the inhalation component generation device according to the thirteenth feature, wherein the plurality of predetermined voltage ranges do not overlap one another.

The fifteenth feature provides the inhalation component generation device according to the thirteenth feature or the fourteenth feature, wherein the control unit is configured to be capable of estimating or detecting at least one of degradation and failure of the power supply based on the value related to the operation amount of the load operated in a period in which the acquired voltage value of the power supply is in a specific voltage range even in the specific voltage range covering one or more of the plurality of predetermined voltage ranges.

The sixteenth feature provides the inhalation component generation device according to the fifteenth feature, wherein the control unit is configured to not perform determination of degradation or failure of the power supply in an irregular range in which a range contributing to the vaporization or atomization of the inhalation component source among the plurality of predetermined voltage ranges is equal to or less than a predetermined ratio or width, and to exclude the irregular range from the specific voltage range.

The seventeenth feature provides the inhalation component generation device according to the fifteenth feature, wherein the control unit is configured to compare the value related to the operation amount of the load operated in a period in which the acquired voltage value of the power supply is in a specific voltage range with a specific threshold even in the specific voltage range covering two or more voltage ranges adjacent to each other among the plurality of predetermined voltage ranges, and to determine that the power supply has been degraded or has failed when the value related to the operation amount of the load is equal to or less than the specific threshold, and the specific threshold is set to be smaller than a total sum of the predetermined thresholds for comparing the operation amounts of the load in the respective two or more voltage ranges.

The eighteenth feature provides the inhalation component generation device according to the seventeenth feature, wherein the control unit is configured not to perform determination of degradation or failure of the power supply in an irregular range in which the range contributing to the vaporization or atomization of the inhalation component source among the plurality of predetermined voltage ranges is equal to or less than a predetermined ratio or width, and to exclude the irregular range from the specific voltage range to subtract, from the specific threshold, a value equal to or less than the predetermined threshold to be compared with the operation amount of the load in the irregular range.

The nineteenth feature provides the inhalation component generation device according to the seventeenth feature, wherein the control unit is configured to, when there is an irregular range in which a range contributing to the vaporization or atomization of the inhalation component source among the plurality of predetermined voltage ranges is equal to or less than a predetermined ratio or width, reduce a predetermined threshold to be compared with the operation amount of the load in an irregular range and the specific threshold.

The twentieth feature provides the inhalation component generation device according to the twelfth feature or the nineteenth feature, wherein the control unit is configured to be capable of acquiring a voltage of the power supply while the load is not operating, and the control unit is configured to correct the predetermined threshold when the voltage of the power supply falls below an upper limit value of the predetermined range without contributing to the vaporization or atomization of the inhalation component source.

The twenty-first feature provides the inhalation component generation device according to the eleventh feature, the twelfth feature, the sixteenth feature or the eighteenth feature, wherein a fact that the range contributing to the vaporization or atomization of the inhalation component source in the predetermined voltage range is equal to or less than a predetermined ratio or width is caused by the power supply being not charged to a fully charged voltage or by prolonged neglect during which the vaporization or atomization of the inhalation component source is not performed by the load.

The twenty-second feature provides the inhalation component generation device according to the eleventh feature, the twelfth feature, the sixteenth feature, the eighteenth feature, or the twenty-first feature, wherein the control unit is configured to measure a time period having elapsed since the vaporization or atomization of the inhalation component source by the load and detect prolonged neglect of the power supply based on the elapsed time period.

The twenty-third feature provides the inhalation component generation device according to the eleventh feature, the twelfth feature, the sixteenth feature, the eighteenth feature, or the twenty-first feature, wherein the control unit is configured to detect prolonged neglect of the power supply based on a voltage change of the power supply after the vaporization or atomization of the inhalation component source by the load.

The twenty-fourth feature provides the inhalation component generation device according to any one of the thirteenth feature to the nineteenth feature, wherein the plurality of predetermined voltage ranges are set to be narrower as the voltage range in which a change in a voltage value of the power supply with respect to the change in a charged amount of the power supply is smaller.

The twenty-fifth feature provides the inhalation component generation device according to any one of the first feature to the twenty-fourth feature, wherein, when the range contributing to the vaporization or atomization of the inhalation component source is equal to or less than a predetermined ratio or width in the predetermined voltage range, the control unit is configured to set a new predetermined voltage range based on the voltage of the power supply contributing to the vaporization or atomization of the inhalation component source after prolonged neglect during which the vaporization or atomization of the inhalation component source is not performed by the load, and the value related to the operation amount of the load operated until the voltage of the power supply is lowered from the voltage to a lower limit value of the predetermined voltage range.

The twenty-sixth feature provides the inhalation component generation device according to any one of the first feature to the tenth feature, the thirteenth feature to the fifteenth feature, and the seventeenth feature, wherein the control unit is configured to integrate, as an integral value, a time in which the voltage of the power supply has dropped without contributing to the vaporization or atomization of the inhalation component source in the predetermined range, and the control unit is configured to add a value obtained by correcting the integral value based on a predetermined relationship to the value related to the operation amount of the load.

The twenty-seventh feature provides the inhalation component generation device according to any one of the first feature to the twenty-sixth feature, wherein the predetermined voltage range is set to a range excluding a plateau range in which a change in voltage value of the power supply with respect to a change in the charged amount of the power supply is smaller than other voltage ranges.

The twenty-eighth feature provides the inhalation component generation device according to the twenty-seventh feature, wherein the plateau range is defined by a range including both of a plateau range in which, in a new state, a change in the voltage value of the power supply with respect to a change in the charged amount of the power supply is smaller than other voltage ranges and a plateau range in which, in a degraded state, a change in the voltage value of the power supply with respect to a change in the charged amount of the power supply is smaller than other voltage ranges.

The twenty-ninth feature provides the inhalation component generation device according to any one of the first feature to the twenty-eighth feature, further including a temperature sensor configured to output a temperature of the power supply, wherein the control unit is configured to be capable of changing or correcting an algorithm for estimating or detecting at least one of the degradation and failure of the power supply, when the temperature of the power supply is lower than a first temperature threshold.

The thirtieth feature provides the inhalation component generation device according to the twenty-ninth feature, wherein the control unit is configured to compare, with a predetermined threshold, the value related to the operation amount of the load operated in the period in which the acquired voltage value of the power supply is in a predetermined voltage range, and to determine that the power supply has been degraded or has failed when the value related to the operation amount of the load is equal to or less than the predetermined threshold, and the control unit is configured to correct to reduce the predetermined threshold when the temperature of the power supply is lower than the first temperature threshold, and to perform the comparison based on the corrected threshold.

The thirty-first feature provides the inhalation component generation device according to any one of the first feature to the thirtieth feature, further including a temperature sensor configured to output a temperature of the power supply, wherein the control unit is configured not to estimate or detect at least one of the degradation or failure of the power supply when the temperature of the power supply is lower than a second temperature threshold.

The thirty-second feature provides the inhalation component generation device according to any one of the first feature to the thirty-first feature, further including a temperature sensor configured to output a temperature of the power supply and a heater configured to heat the power supply, wherein the control unit is configured to heat the power supply by control of the heater when the temperature of the power supply is lower than a third temperature threshold.

The thirty-third feature provides a method of controlling an inhalation component generation device including a load configured to vaporize or atomize an inhalation component source with electric power from a power supply, the method including the steps of acquiring a voltage value of the power supply, and estimating or detecting at least one of degradation and failure of the power supply based on a value related to an operation amount of the load operated in a period in which the acquired voltage value of the power supply is in a predetermined voltage range.

The thirty-fourth feature provides an inhalation component generation device including a load configured to vaporize or atomize an inhalation component source with electric power from a power supply, and a control unit configured to be capable of acquiring a value related to an operation amount of the load and a voltage value of the power supply, wherein the control unit is configured to be capable of estimating or detecting at least one of degradation and failure of the power supply based on a voltage of the power supply changed in a period in which the acquired value related to the operation amount of the load is in a predetermined range.

The thirty-fifth feature provides a method of controlling an inhalation component generation device including a load configured to vaporize or atomize an inhalation component source with electric power from a power supply, the method including the steps of acquiring a value related to an operation amount of the load, and estimating or detecting at least one of degradation and failure of the power supply based on a voltage of the power supply changed in a period in which the acquired value related to the operation amount of the load is in a predetermined range.

The thirty-sixth feature provides a program causing an inhalation component generation device to execute the method according to the thirty-third feature or the thirty-fifth feature.

DESCRIPTION OF EMBODIMENTS

Figure 1:
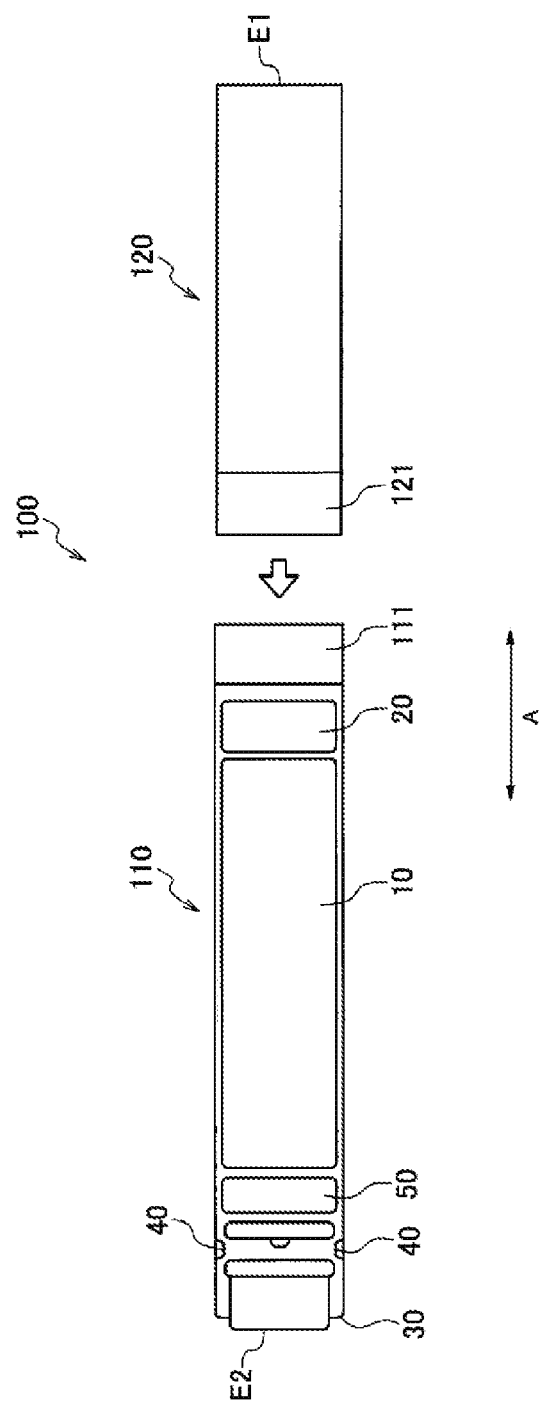
FIG. 1 is a schematic diagram illustrating an inhalation component generation device according to one embodiment.

Hereinafter, embodiments will be described. Note that the same or similar parts are denoted by the same or similar reference signs in the description of the drawings below. However, it should be noted that the drawings are schematic and ratios in dimensions may be different from actual ones.

Therefore, specific dimensions and the like should be determined with reference to the following description. Moreover, it is a matter of course that parts having different dimensional relationships and ratios may be included between the mutual drawings.

[Outline of Disclosure]

It is important to estimate or detect the degradation of a chargeable and dischargeable power supply for the safety of the device and the more accurate control. However, it is difficult to accurately diagnose the degraded state of the power supply. Particularly in the inhalation component generation device having no complicated control circuit, the complicate electrical control is difficult, and no attempt is made to estimate or detect the degraded state of the power supply.

An inhalation component generation device according to one aspect includes a load configured to vaporize or atomize an inhalation component source with electric power from a power supply, and a control unit configured to be capable of acquiring a value related to an operation amount of the load and a voltage value of the power supply. The control unit is configured to be capable of estimating or detecting at least one of degradation and failure of the power supply based on the value related to the operation amount of the load operated in a period in which the acquired voltage value of the power supply is in a predetermined voltage range.

A method of controlling an inhalation component generation device according to one aspect relates to a method of controlling an inhalation component generation device including a load configured to vaporize or atomize an inhalation component source with electric power from a power supply. The method includes the steps of acquiring a voltage value of the power supply, and estimating or detecting at least one of degradation and failure of the power supply based on the value related to an operation amount of the load operated in a period in which the acquired voltage value of the power supply is in a predetermined voltage range.

A possible range of an output voltage value of the power supply is substantially constant regardless of the degraded state of the power supply. However, a voltage of the degraded power supply decreases rapidly together with the discharge of the electric power as compared with a new power supply. In view of such power supply characteristics, an operation amount of the load that is capable of operating in a period in which the acquired voltage value of the power supply is in a predetermined voltage range differs between a new power supply and the degraded power supply.

Accordingly, according to an inhalation component generation device according to the above-described aspect and a method of controlling the inhalation component generation device, it becomes possible to estimate or detect at least one of degradation and failure of the power supply based on the value related to the operation amount of the load operated in a period in which the acquired voltage value of the power supply is in a predetermined voltage range.

An inhalation component generation device according to one aspect includes a load configured to vaporize or atomize an inhalation component source with electric power from a power supply, and a control unit configured to be capable of acquiring a value related to an operation amount of the load and a voltage value of the power supply. The control unit is configured to be capable of estimating or detecting at least one of degradation and failure of the power supply based on a difference in voltage of the power supply changed in a period in which the acquired value related to the operation amount of the load is in a predetermined range.

A method of controlling of an inhalation component generation device according to one aspect relates to a method of controlling an inhalation component generation device including a load configured to vaporize or atomize an inhalation component source with electric power from a power supply. The method includes the steps of acquiring a value related to an operation amount of the load, and estimating or detecting at least one of degradation and failure of the power supply based on a difference in voltage of the power supply changed in a period in which the acquired value related to the operation amount of the load is in a predetermined range.

In view of the above-described power supply characteristics, a voltage range of the power supply changed in a period in which the acquired value related to the operation amount of the load is in a predetermined range differs between a new power supply and the degraded power supply. Accordingly, it is possible to estimate or detect at least one of degradation and failure of the power supply based on a difference in voltage of the power supply changed in a period in which the acquired value related to the operation amount of the load is in a predetermined range.

According to the above-described aspect, the degradation or failure of the power supply can be estimated or detected based on the voltage value of the power supply and the operation amount of the load, so that there can be obtained an advantage that another additional sensor is unnecessary. That is, at least one of degradation and failure of the power supply can be estimated or detected with a minimum of sensor types. However, the inhalation component generation device may include other additional sensors that acquire other parameters different from the voltage value of the power supply and the operation amount of the load.

First Embodiment (Inhalation Component Generation Device)

Figure 2:
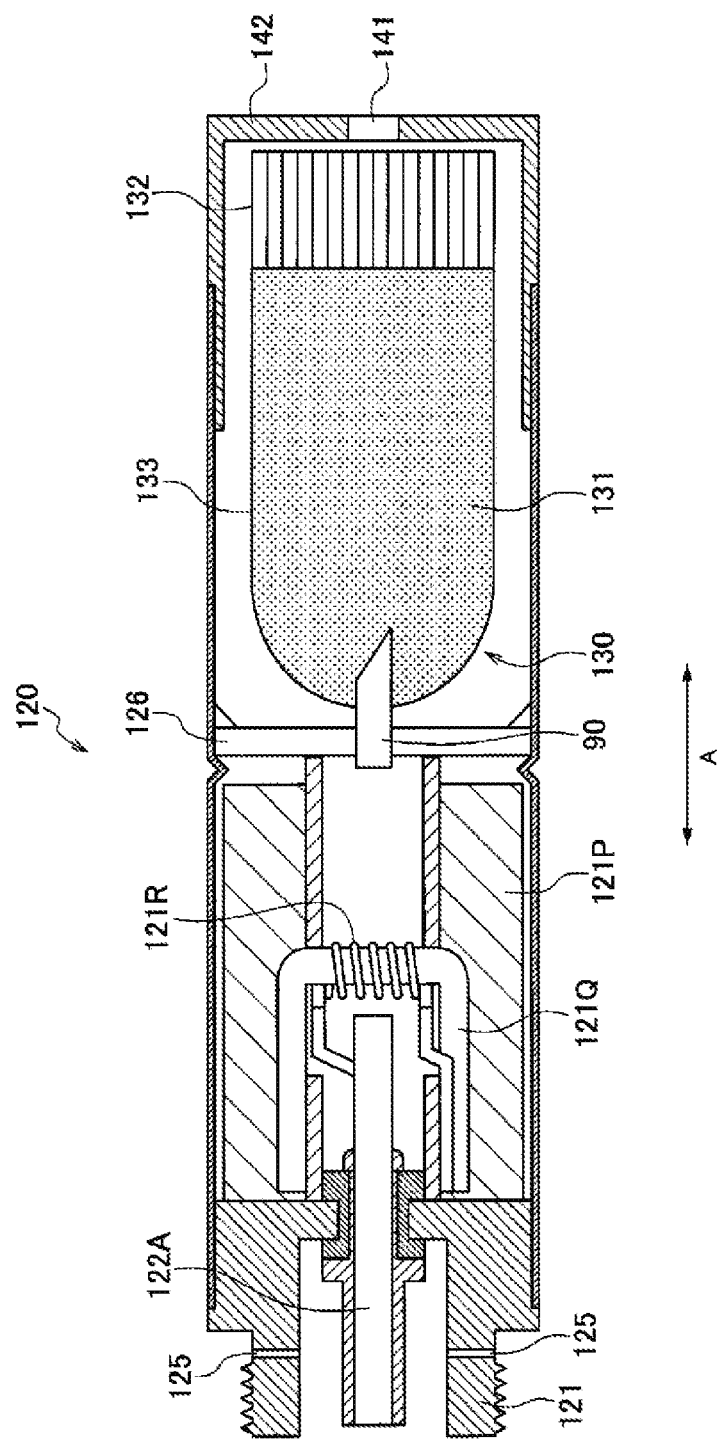
FIG. 2 is a schematic diagram illustrating an atomizing unit according to one embodiment.
Figure 3:
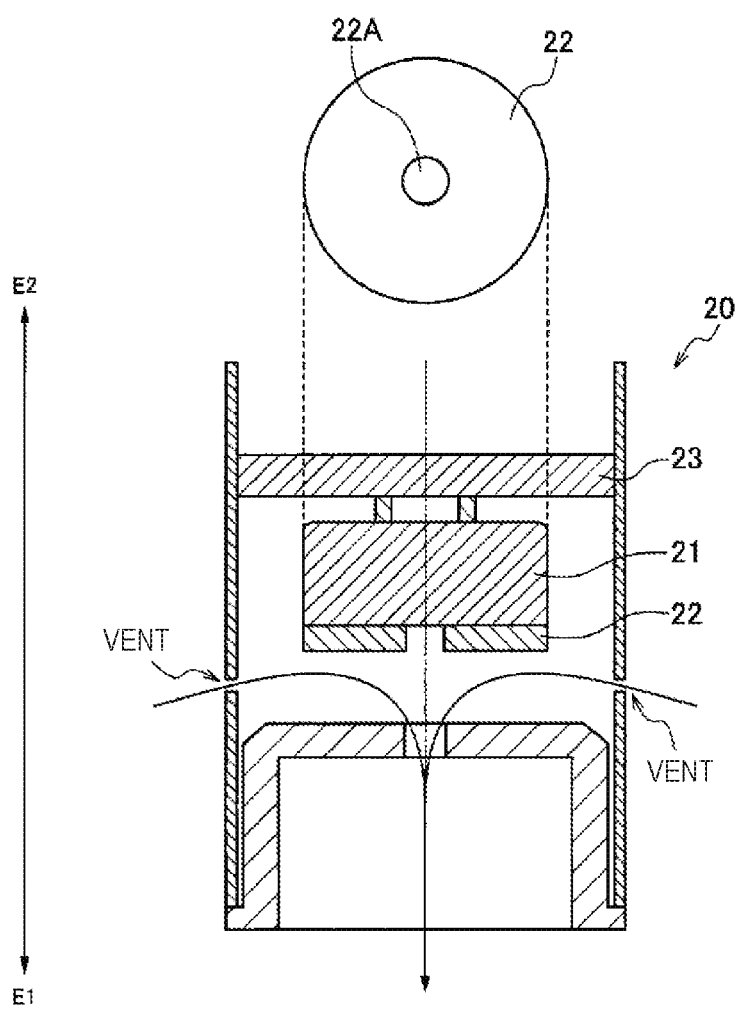
FIG. 3 is a schematic diagram illustrating an example of a configuration of an inhalation sensor according to one embodiment.
Figure 4:
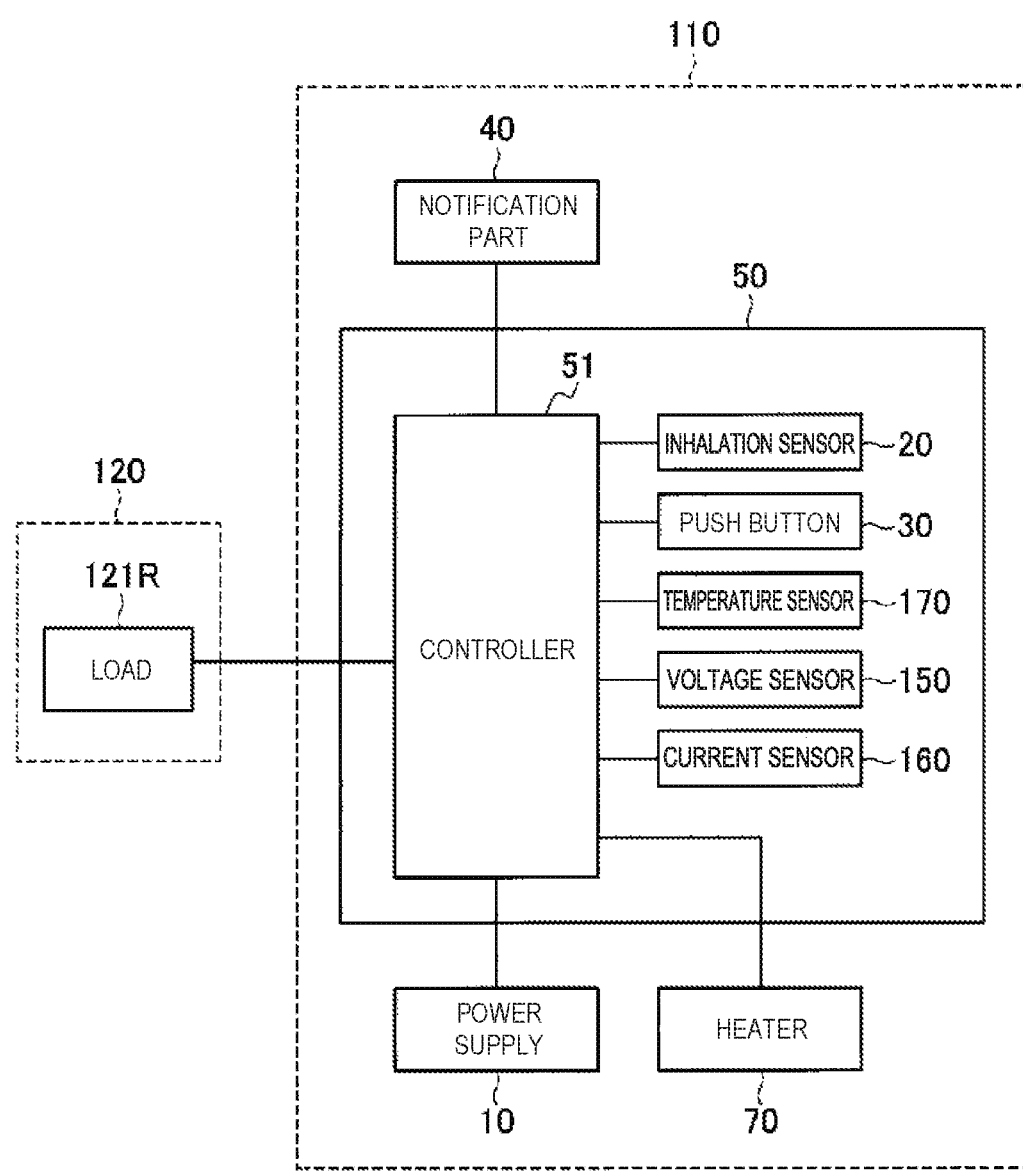
FIG. 4 is a block diagram illustrating the inhalation component generation device.
Figure 5:
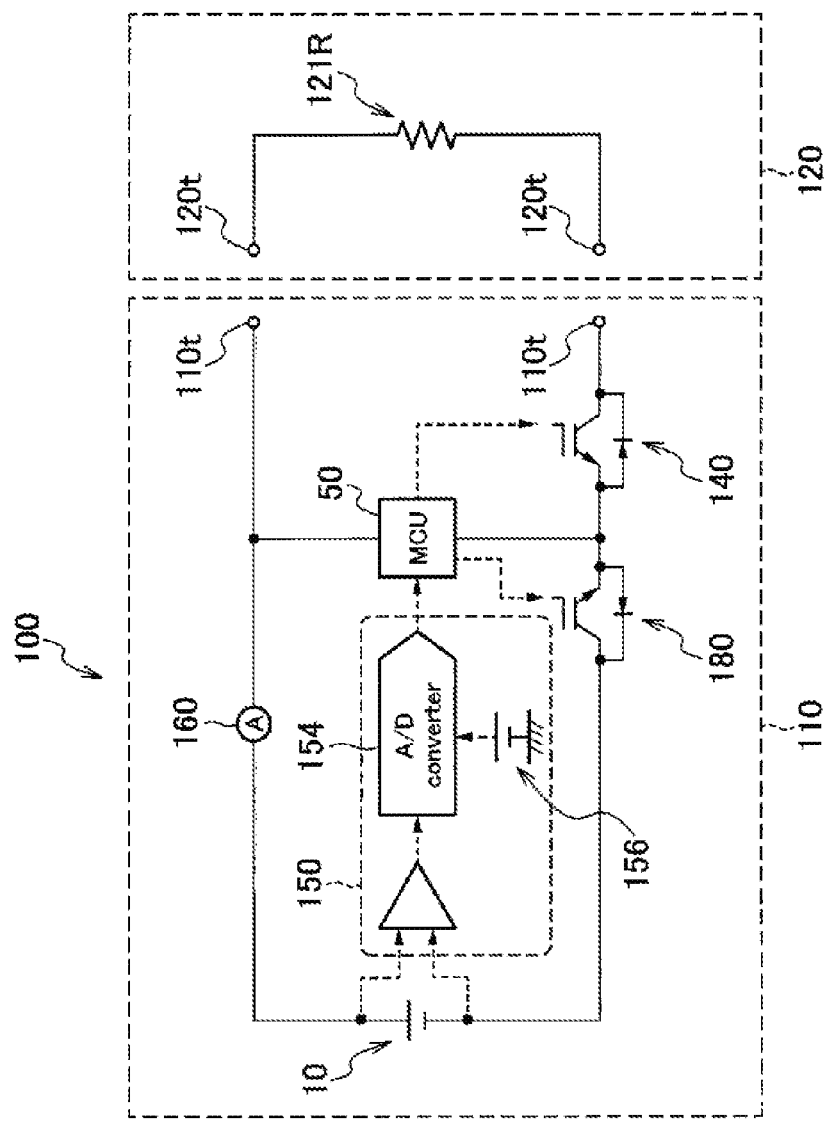
FIG. 5 is a diagram illustrating an electrical circuit of an atomizing unit and an electrical unit.
Figure 6:
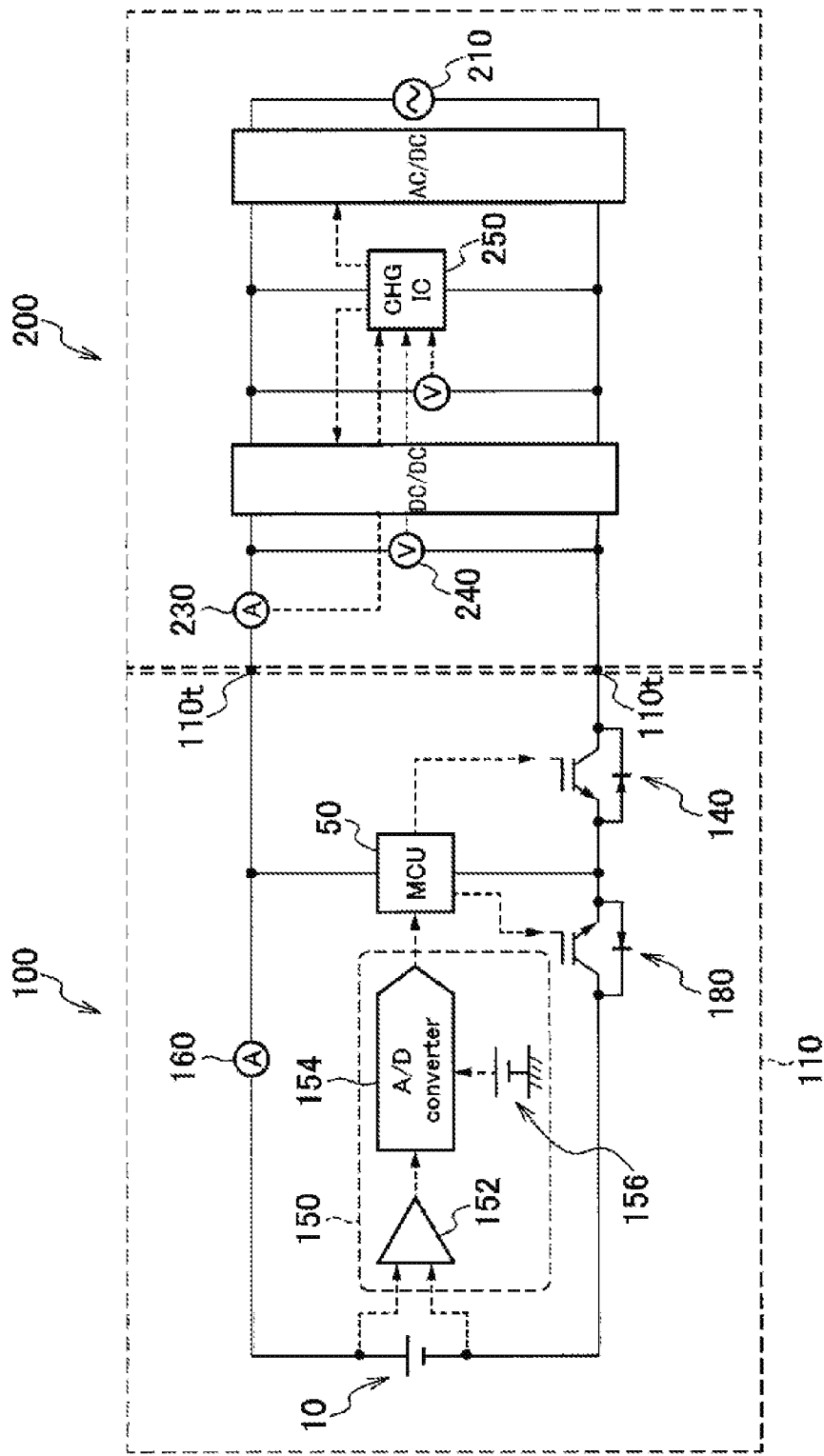
FIG. 6 is a diagram illustrating an electrical circuit of a charger and the electrical unit in a state in which the charger is connected.

Hereinafter, an inhalation component generation device according to a first embodiment will be described. FIG. 1 is an exploded view illustrating an inhalation component generation device according to one embodiment. FIG. 2 is a diagram illustrating an atomizing unit according to one embodiment. FIG. 3 is a schematic diagram illustrating an example of a configuration of an inhalation sensor according to one embodiment. FIG. 4 is a block diagram illustrating an electric configuration of the inhalation component generation device. FIG. 5 is a diagram illustrating an electrical circuit of the atomizing unit and an electrical unit. FIG. 6 is a diagram illustrating an electrical circuit of a charger and the electrical unit in a state in which the charger is connected.

An inhalation component generation device 100 may be a non-combustion-type flavor inhaler for inhaling an inhalation component (an inhaling flavor component) without combustion. The inhalation component generation device 100 may have a shape extending along a predetermined direction A which is a direction from a non-inhalation port end E2 toward an inhalation port end E1. In this case, the inhalation component generation device 100 may include one end E1 having an inhalation port 141 for inhaling an inhalation component and the other end E2 opposite to the inhalation port 141.

The inhalation component generation device 100 may include an electrical unit 110 and an atomizing unit 120. The atomizing unit 120 may be configured to be detachably attached to the electrical unit 110 through mechanical connection parts 111 and 121. When the atomizing unit 120 and the electrical unit 110 are mechanically connected to each other, a load 121R (described later) in the atomizing unit 120 is electrically connected to a power supply 10 provided in the electrical unit 110 through electrical connection terminals 110t and 120t. That is, the electrical connection terminals 110t and 120t form a connection part capable of electrically disconnecting and connecting the load 121R from/to the power supply 10.

The atomizing unit 120 includes an inhalation component source to be inhaled by a user, and the load 121R configured to vaporize or atomize the inhalation component source with electric power from the power supply 10. The inhalation component source may include an aerosol source that generates aerosol and/or a flavor source that generates a flavor component.

The load 121R may be any element capable of generating aerosol and/or a flavor component from an aerosol source and/or a flavor source by receiving the electric power. The load 121R may be, for example, a heat generating element such as a heater or an element such as an ultrasound generator. Examples of the heat generating element include a heat generation resistor, a ceramic heater, and an induction heating type heater.

Hereinafter, a more detailed example of the atomizing unit 120 will be described with reference to FIG. 1 and FIG. 2. The atomizing unit 120 may include a reservoir 121P, a wick 121Q, and the load 121R. The reservoir 121P may be configured to store a liquid aerosol source or flavor source. The reservoir 121P may be, for example, a porous body made of a material such as a resin web. The wick 121Q may be a liquid holding member that draws the aerosol source or the flavor source from the reservoir 121P using capillary action. The wick 121Q may be made of, for example, glass fiber or porous ceramic.

The load 121R atomizes the aerosol source held by the wick 121Q or heats the flavor source held by the wick 121Q. The load 121R is formed of, for example, a resistive heating element (for example, a heating wire) wound around the wick 121Q.

The air that has flowed in from an inlet hole 122A passes through the vicinity of the load 121R in the atomizing unit 120. The inhalation component generated by the load 121R flows together with the air toward the inhalation port.

The aerosol source may be a liquid at ordinary temperature. For example, polyhydric alcohol such as glycerin and propylene glycol, water or the like may be used as the aerosol source. The aerosol source itself may contain the flavor component. Alternatively, the aerosol source may include a tobacco raw material that emits an inhaling flavor component by being heated or an extract deriving from the tobacco raw material.

Note that, although an example of the liquid aerosol source at ordinary temperature has been described in detail in the above-described embodiment, an aerosol source that is a solid at ordinary temperature may be also used instead of the liquid aerosol source.

The atomizing unit 120 may include a replaceable flavor unit (cartridge) 130. The flavor unit 130 includes a cylindrical body 131 that accommodates the flavor source. The cylindrical body 131 may include a membrane member 133 and a filter 132. The flavor source may be provided in a space formed by the membrane member 133 and the filter 132.

The atomizing unit 120 may include a breaking part 90. The breaking part 90 is a member for breaking a part of the membrane member 133 of the flavor unit 130. The breaking part 90 may be held by a partition wall member 126 for partitioning into the atomizing unit 120 and the flavor unit 130. The partition wall member 126 is made of, for example, a polyacetal resin. The breaking part 90 is, for example, a cylindrical hollow needle. An airflow path that pneumatically communicates between the atomizing unit 120 and the flavor unit 130 is formed by puncturing the membrane member 133 with a tip of the hollow needle. Here, it is preferable that an inside of the hollow needle is provided with a mesh having a roughness of not allowing the flavor source to pass through.

According to an example of the preferred embodiment, the flavor source in the flavor unit 130 imparts the inhaling flavor component to the aerosol generated by the load 121R of the atomizing unit 120. The flavor imparted to the aerosol by the flavor source is sent to the inhalation port of the inhalation component generation device 100. Thus, the inhalation component generation device 100 may have a plurality of inhalation component sources. Alternatively, the inhalation component generation device 100 may have only one inhalation component source.

The flavor source in the flavor unit 130 may be a solid at ordinary temperature. By way of example, the flavor source comprises an ingredient piece of a plant material which imparts the inhaling flavor component to the aerosol. Shredded tobacco or a forming body obtained by forming a tobacco material such as a tobacco raw material in a granular form, may be used as an ingredient piece which is a component of the flavor source.

Alternatively, the flavor source may comprise a forming body obtained by forming a tobacco material into a sheet form. Also, the ingredient piece, which is a component of the flavor source, may comprise a plant (for example, mint, a herb, and the like) other than tobacco. The flavor source may be provided with flavor such as menthol.

The inhalation component generation device 100 may include a mouthpiece 142 having the inhalation port 141 through which a user inhales the inhalation component. The mouthpiece 142 may be configured to be detachably attached to the atomizing unit 120 or the flavor unit 130, or may be configured to be an integral part of the atomizing unit 120 or the flavor unit 130.

The electrical unit 110 may include the power supply 10, a notification part 40, and a control unit 50. The power supply 10 stores the electric power necessary for the operation of the flavor inhaler 100. The power supply 10 may be detachably attached to the electrical unit 110. The power supply 10 may be, for example, a rechargeable battery such as a lithium ion secondary battery.

The control unit 50 may include, for example, a controller 51 such as a microcontroller, an inhalation sensor 20, and a push button 30. In addition, the inhalation component generation device 100 may include a voltage sensor 150, a current sensor 160, and a temperature sensor 170, where appropriate. The controller 51 performs various types of control necessary for the operation of the inhalation component generation device 100 according to the output values from the voltage sensor 150, the current sensor 160, and the temperature sensor 170. For example, the controller 51 may constitute a power control unit that controls the electric power from the power supply 10 to the load 121R.

When the atomizing unit 120 is connected to the electrical unit 110, the load 121R provided in the atomizing unit 120 is electrically connected to the power supply 10 of the electrical unit 110 (see FIG. 5).

The inhalation component generation device 100 may include a switch 140 capable of electrically connecting and disconnecting the load 121R to or from the power supply 10. The switch 140 is opened or closed by the control unit 50. The switch 140 may be comprised of, for example, a MOSFET.

When the switch 140 is turned on, the electric power is supplied from the power supply 10 to the load 121R. On the other hand, when the switch 140 is turned off, the supply of the electric power from the power supply 10 to the load 121R is stopped. The turning on and off of the switch 140 is controlled by the control unit 50.

The control unit 50 may include a request sensor capable of outputting a signal requesting the operation of the load 121R. The request sensor may be, for example, a push button 30 to be pressed by a user, or the inhalation sensor 20 configured to detect a user's inhaling operation. The control unit 50 acquires an operation request signal to the load 121R and generates a command for operating the load 121R. In a specific example, the control unit 50 outputs the command for operating the load 121R to the switch 140, and the switch 140 is turned on according to this command. Thus, the control unit 50 is configured to control the supply of the electric power from the power supply 10 to the load 121R. When the electric power is supplied from the power supply 10 to the load 121R, the inhalation component source is vaporized or atomized by the load 121R.

In addition, the inhalation component generation device 100 may include a stop part 180 configured to shut off or reduce a charging current to the power supply 10, where appropriate. The stop part 180 may be comprised of, for example, a MOSFET switch. The control unit 50 can turn off the stop part 180 to forcibly shut off or reduce the charging current to the power supply 10, even if the electrical unit 110 is connected to a charger 200. Note that even if a dedicated stop part 180 is not necessarily provided, the control unit 50 can turn off the switch 140 to forcibly shut off or reduce the charging current to the power supply 10.

The voltage sensor 150 may be configured to output a voltage of the power supply 10. The control unit 50 can obtain an output value of the voltage sensor 150. That is, the control unit 50 is configured to be capable of acquiring a voltage value of the power supply 10.

The current sensor 160 may be configured to be capable of detecting an amount of current that has flowed out from the power supply 10 and an amount of current that has flowed into the power supply 10. The temperature sensor 170 may be configured to be capable of outputting a temperature of the power supply 10, for example. The control unit 50 is configured to be capable of acquiring outputs of the voltage sensor 150, the current sensor 160, and the temperature sensor 170. The control unit 50 performs various types of control using these outputs.

The inhalation component generation device 100 may include a heater 70 configured to heat the power supply 10, where appropriate. The heater 70 may be provided in the vicinity of the power supply 10, and is configured to be operable according to a command from the control unit 50.

The inhalation sensor 20 may be configured to output an output value that varies depending on inhalation from the inhalation port. Specifically, the inhalation sensor 20 may be a sensor that outputs a value (for example, a voltage value or a current value) that changes according to the flow rate of air (i.e., a user's puff operation) inhaled from the non-inhalation port side toward the inhalation port side. Examples of such a sensor include a condenser microphone sensor, and a known flow sensor.

FIG. 3 illustrates a specific example of the inhalation sensor 20. The inhalation sensor 20 illustrated in FIG. 3 includes a sensor body 21, a cover 22, and a substrate 23. The sensor body 21 is comprised of, for example, a capacitor. An electric capacity of the sensor body 21 changes due to vibration (pressure) generated by air inhaled from an air introduction hole 125 (i.e., air inhaled from the non-inhalation port side toward the inhalation port side). The cover 22 is provided on the inhalation port side with respect to the sensor body 21, and has an opening 22A. Providing the cover 22 having the opening 22A allows the electric capacity of the sensor body 21 to be changed easily, and improves the response characteristic of the sensor body 21. The substrate 23 outputs a value (here, a voltage value) indicating the electric capacity of the sensor body 21 (capacitor).

The inhalation component generation device 100, more specifically, the electrical unit 110 may be configured to be connectable to the charger 200 for charging the power supply 10 in the electrical unit 110 (see FIG. 6). When the charger 200 is connected to the electrical unit 110, the charger 200 is electrically connected to the power supply 10 of the electrical unit 110.

The electrical unit 110 may include a determination part configured to determine whether the charger 200 is connected. The determination part may be, for example, means for determining the presence or absence of connection of the charger 200 based on a change in potential difference between a pair of electrical terminals to which the charger 200 is connected. The determination part is not limited to this means, and may be any means that can determine the presence or absence of the connection of the charger 200.

The charger 200 includes an external power supply 210 for charging the power supply 10 in the electrical unit 110. A pair of electrical terminals 110t of the electrical unit 110 for electrically connecting the charger 200 can also serve as a pair of electrical terminals of the electrical unit 110 for electrically connecting the load 121R.

When the external power supply 210 is an AC power supply, the charger 200 may include an inverter configured to convert alternating current to direct current. The charger 200 may include a processor 250 configured to control the charging of the power supply 10. Furthermore, the charger 200 may include an ammeter 230 and a voltmeter 240, where appropriate. The ammeter 230 acquires a charging current to be supplied from the charger 200 to the power supply 10. The voltmeter 240 acquires a voltage between the pair of electrical terminals to which the charger 200 is connected. The processor 250 of the charger 200 uses the output value from the ammeter 230 and/or the voltmeter 240 to control the charging of the power supply 10. In addition, the charger 200 may further include a voltage sensor configured to acquire a direct-current voltage output from the inverter, and a converter capable of boosting and/or stepping down the direct-current voltage output by the inverter.

To simplify the structure of the inhalation component generation device 100, the processor 250 of the charger 200 may be configured to be incapable of communicating with the control unit 50 of the electrical unit 110. That is, a communication terminal for communicating between the processor 250 of the charger 200 and the control unit 50 is unnecessary. In other words, in the connection interface with the charger 200, the electrical unit 110 has only two electrical terminals, one for a main positive bus and the other for a main negative bus.

The notification part 40 issues notification for notifying a user of various types of information. The notification part 40 may be, for example, a light emitting element such as an LED. Instead of this, the notification part 40 may be an element that generates sound, or a vibrator.

The notification part 40 may be configured to notify a user when a remaining amount of the power supply 10 is low but is not insufficient and when the remaining amount of the power supply 10 is insufficient, based on the voltage of the power supply 10. For example, when the remaining amount of the power supply 10 is insufficient, the notification part 40 issues notification different from that when the remaining amount of the power supply 10 is not insufficient. For example, when the voltage of the power supply 10 is in the vicinity of a discharge termination voltage, the remaining amount of the power supply 10 can be determined to be insufficient.

(Power Supply Mode)

Figure 7:
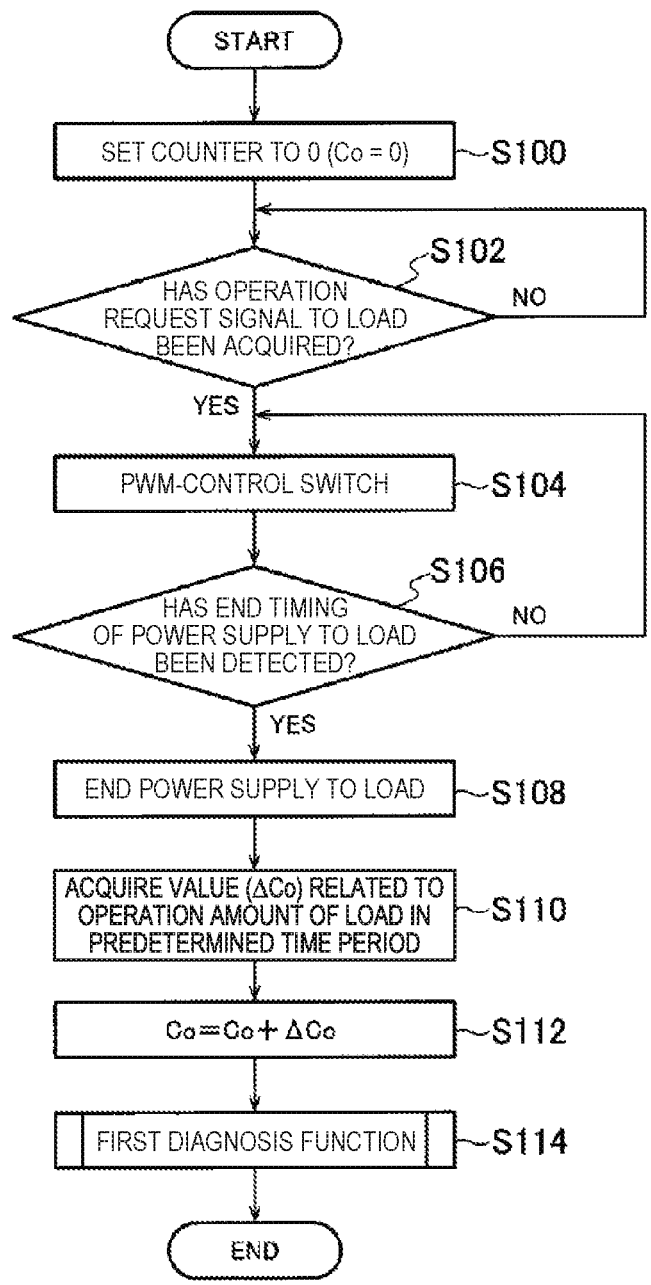
FIG. 7 is a flowchart illustrating an example of a control method in a power supply mode of the inhalation component generation device.

FIG. 7 is a flowchart illustrating a control method in a power supply mode according to one embodiment. The power supply mode is a mode in which electric power can be supplied from the power supply 10 to the load 121R. The power supply mode can be performed at least when the atomizing unit 120 is connected to the electrical unit 110.

The control unit 50 sets a counter (Co) that measures a value related to the operation amount of the load to "0" (step S100), and determines whether to have acquired the operation request signal to the load 121R (step S102). The operation request signal may be a signal acquired from the inhalation sensor 20 when the inhalation sensor 20 detects the user's inhaling operation. That is, the control unit 50 may perform a pulse width modulation (PWM) control with respect to the switch 140 when the user's inhaling operation has been detected by the inhalation sensor 20 (step S104). Alternatively, the operation request signal may be a signal acquired from the push button 30 when it is detected that the push button 30 has been pressed by the user. That is, when the control unit 50 detects that the user has pressed the push button, the control unit 50 may perform the PWM control with respect to the switch 140 (step S104). Note that in step S104, a pulse frequency modulation (PFM) control may be performed instead of the PWM control. A duty ratio in the PWM control and a switching frequency in the PFM control may be adjusted by various parameters such as a voltage of the power supply 10 acquired by the voltage sensor 150.

When the PWM control is performed with respect to the switch 140 by the control unit 50, aerosol is generated.

The control unit 50 determines whether to have detected an end timing of the power supply to the load 121R (step S106). When detecting the end timing, the control unit 50 ends the power supply to the load (step S108). When the control unit 50 ends the power supply to the load (step S108), the control unit 50 acquires a value (ΔCo) related to the operation amount of the load 121R (step S110). This acquired value (ΔCo) related to the operation amount of the load 121R is a value in a period between steps S104 and S108. The value (ΔCo) related to the operation amount of the load 121R may be, for example, an amount of electric power supplied to the load 121R for a predetermined time, i.e., in the period between steps S104 and S108, an operation time of the load 121R, or a consumption amount of the inhalation component source consumed for the predetermined time.

Next, the control unit 50 acquires an accumulated value "Co=Co+ΔCo" of the value related to the operation amount of the load 121R (step S112). Then, the control unit 50 performs a first diagnostic function (step S114) as necessary.

The end timing of the power supply to the load 121R may be a timing when the inhalation sensor 20 detects the end of the operation for using the load 121R. For example, the end timing of the power supply to the load 121R may be a timing when the inhalation sensor 20 detects the end of the user's inhaling operation. Instead of this, the end timing of the power supply to the load 121R may be a timing when the control unit 50 detects the release of the pressing of the push button 30. Furthermore, the end timing of the power supply to the load 121R may be a timing when the control unit 50 detects that a predetermined cut-off time has elapsed since the start of the power supply to the load 121R. The predetermined cut-off time may be preset based on a period required for a general user to perform one inhaling operation. For example, the predetermined cut-off time may be in a range of 1 to 5 seconds, preferably 1.5 to 3 seconds, and more preferably 1.5 to 2.5 seconds.

If the control unit 50 does not detect the end timing of the power supply to the load 121R, the control unit 50 performs the PWM control with respect to the switch 140 again, and continues the power supply to the load 121R (step S104). Then, when the control unit 50 detects the end timing of the power supply to the load 121R, the control unit 50 acquires the value related to the operation amount of the load 121R

(step S110), and derives the accumulated value of the value related to the operation amount of the load 121R (step S112).

In this way, when the power supply to the load ends (step S108), the control unit 50 can acquire the value related to the operation amount of the load 121R in a period from the acquisition of the operation request signal to the load until the end timing of the power supply to the load 121R, i.e., in one puff operation. The operation amount of the load 121R in one puff operation may be, for example, an amount of electric power supplied to the load 121R in one puff operation. Instead of this, the operation amount of the load 121R in one puff operation may be, for example, the operation time of the load 121R in one puff operation. The operation time of the load 121R may be the total sum of power pulses supplied to the load 121R in one puff operation (also see FIG. 8), or may be a time period required for one puff operation, i.e., a time period from the acquisition of the operation request signal to the load 121R until the end timing of the power supply to the load 121R is detected. Furthermore, the operation amount of the load 121R in one puff operation may be a consumption amount of the inhalation component source consumed in one puff operation. The consumption amount of the inhalation component source can be estimated from the amount of electric power supplied to the load 121R, for example. When the inhalation component source is a liquid, the consumption amount of the inhalation component source can be acquired by a sensor configured to measure a weight of the inhalation component source remaining in the reservoir or a height of the liquid level of the inhalation component source. In addition, the operation amount of the load 121R in one puff operation may be a temperature of the load 121R, for example, a maximum temperature of the load 121R in one puff operation, or a heat quantity generated in the load 121R. The temperature and the heat quantity of the load 121R can be acquired or estimated using the temperature sensor, for example.

Figure 8:
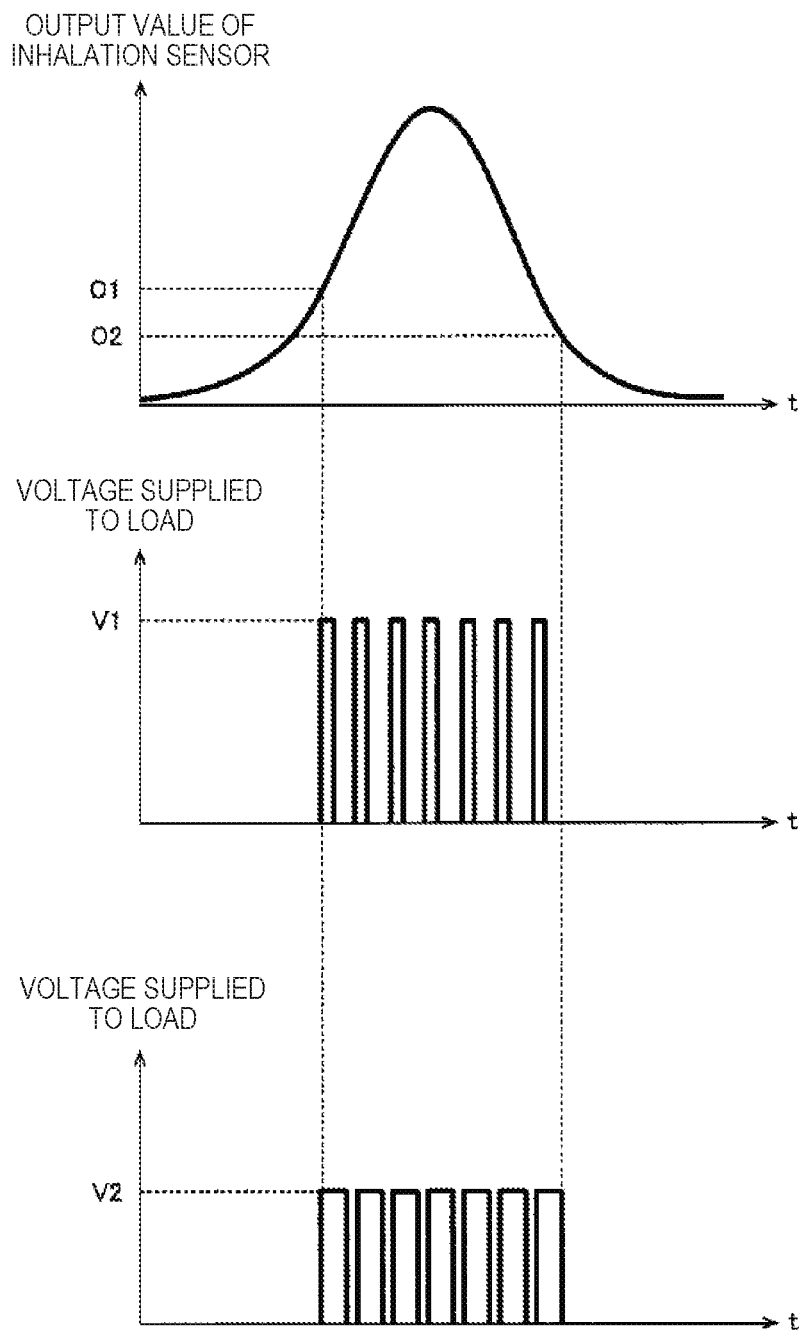
FIG. 8 is a graph showing an example of control of an amount of electric power supplied from a power supply to a load.

FIG. 8 is a graph showing an example of control of an amount of electric power supplied from the power supply 10 to the load 121R. FIG. 8 shows a relationship between an output value of the inhalation sensor 20 and a voltage to be supplied to the load 121R.

The inhalation sensor 20 is configured to output an output value that varies depending on inhalation from the inhalation port 141. The output value of the inhalation sensor 20 may be a value (for example, a value indicating a pressure change in the inhalation component generation device 100) according to a flow velocity and a flow rate of the gas in the flavor inhaler as shown in FIG. 8, but is not necessarily limited thereto.

When the inhalation sensor 20 outputs an output value that varies depending on inhalation, the control unit 50 may be configured to detect the inhalation according to the output value of the inhalation sensor 20. For example, the control unit 50 may be configured to detect the user's inhaling operation when the output value of the inhalation sensor 20 is equal to or larger than a first predetermined value O1. Accordingly, the control unit 50 may determine to have acquired the operation request signal to the load 121R when the output value of the inhalation sensor 20 has become equal to or larger than the first predetermined value O1 (step S102). On the other hand, the control unit 50 may determine to have detected the end timing of the power supply to the load 121R when the output value of the inhalation sensor 20 has become equal to or smaller than a second predetermined value O2 (step S106). In this way, the control unit 50 may be configured to be capable of deriving a value related to the operation amount of the load 121R, for example, the total time to supply electric power to the load 121R in one puff operation, based on the output of the inhalation sensor 20. More specifically, the control unit 50 is configured to be capable of deriving a value related to the operation amount of the load 121R based on at least one of the detected inhalation period and inhalation amount.

Here, the control unit 50 is configured to detect the inhalation only when an absolute value of the output value of the inhalation sensor 20 is equal to or larger than the first predetermined value (predetermined threshold) O1. This can prevent the load 121R from operating due to the noise of the inhalation sensor 20. In addition, since the second predetermined value O2 for detecting the end timing of the power supply to the load 121R is a value for performing the transition from a state in which the load 121R is already operating to a state in which the load 121R is not operating, the second predetermined value O2 may be smaller than the first predetermined value O1. This is because false operation of the load 121R due to picking up of noise of the inhalation sensor 20 like the first predetermined value O1, i.e., the transition from the state in which the load 121R is not operating to the state in which the load 121R is operating cannot occur.

Furthermore, the control unit 50 may include a power control unit configured to control an amount of electric power supplied from the power supply 10 to the load 121R. The power control unit adjusts, for example, the amount of electric power from the power supply 10 to be supplied to the load 121R by the pulse width modulation (PWM) control. The duty ratio relating to the pulse width may be a value smaller than 100%. Note that the power control unit may control an amount of electric power to be supplied from the power supply 10 to the load 121R by the pulse frequency modulation (PFM) control instead of the pulse width modulation control.

For example, when the voltage value of the power supply 10 is relatively high, the control unit 50 narrows the pulse width of the voltage to be supplied to the load 121R (see a middle graph in FIG. 8). For example, when the voltage value of the power supply 10 is relatively low, the control unit 50 widens the pulse width of the voltage to be supplied to the load 121R (see a lower graph in FIG. 8). The control of the pulse width can be performed, for example, by adjusting the length of time from turning on of the switch 140 to turning off of the switch 140. Since the voltage value of the power supply 10 decreases with reduction in a charge amount of the power supply, the amount of electric power is adjusted according to the voltage value. When the control unit 50 thus performs the pulse width modulation (PWM) control, an effective value of the voltage supplied to the load 121R is about the same in both cases where the voltage of the power supply 10 is relatively high and relatively low.

As described above, it is preferable that the power control unit is configured to control the voltage to be applied to the load 121R in the pulse width modulation (PWM) control having a duty ratio that increases as the voltage value of the power supply 10 decreases. This enables an amount of aerosol generated during the puff operation to be substantially equalized regardless of the remaining amount of the power supply 10. More preferably, the power control unit preferably controls the duty ratio of the pulse width modulation (PWM) control so that an amount of electric power per pulse supplied to the load 121R becomes constant.

(First Diagnostic Function)

Figure 9:
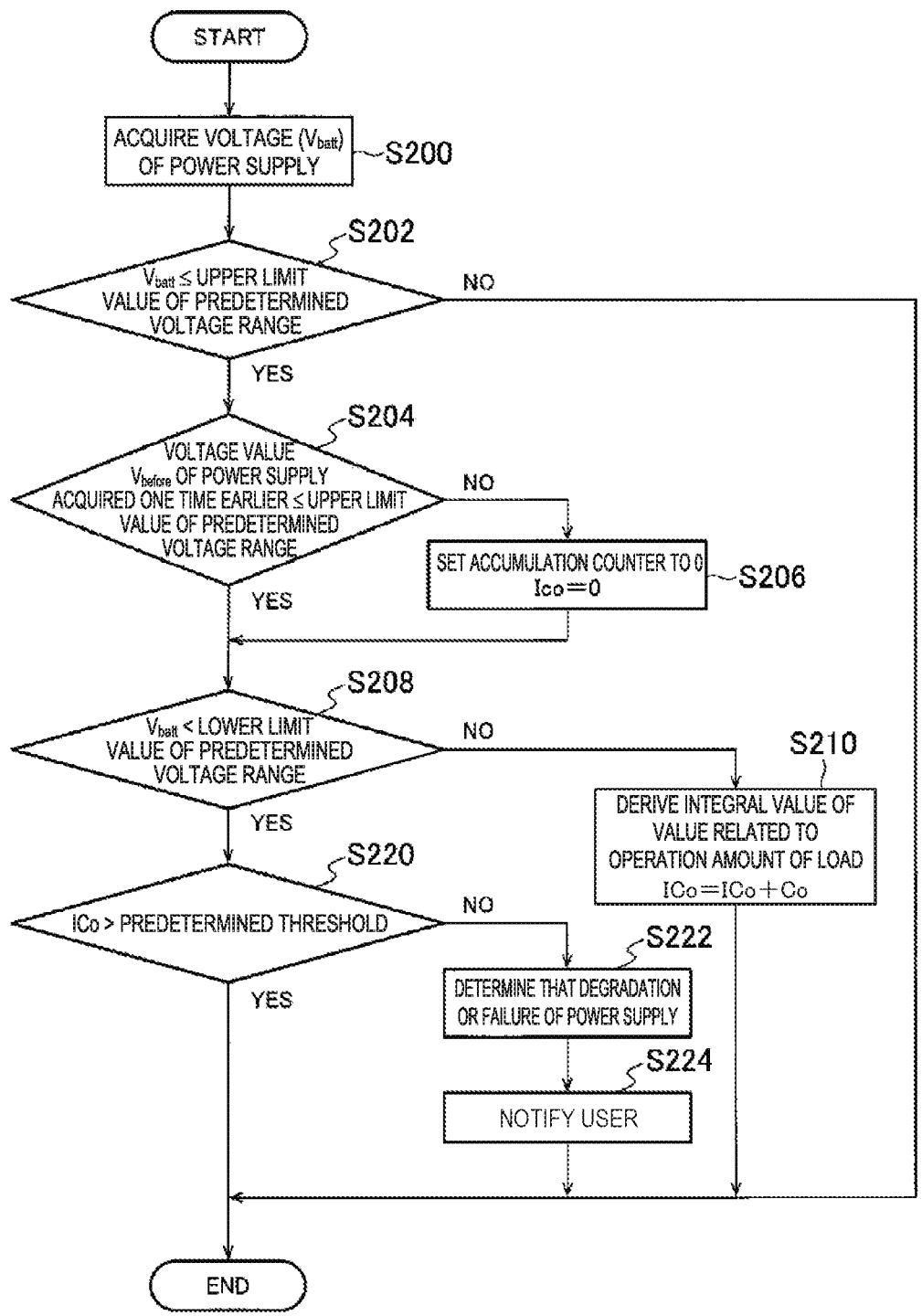
FIG. 9 is a flowchart illustrating an example of a first diagnostic processing.
Figure 10:
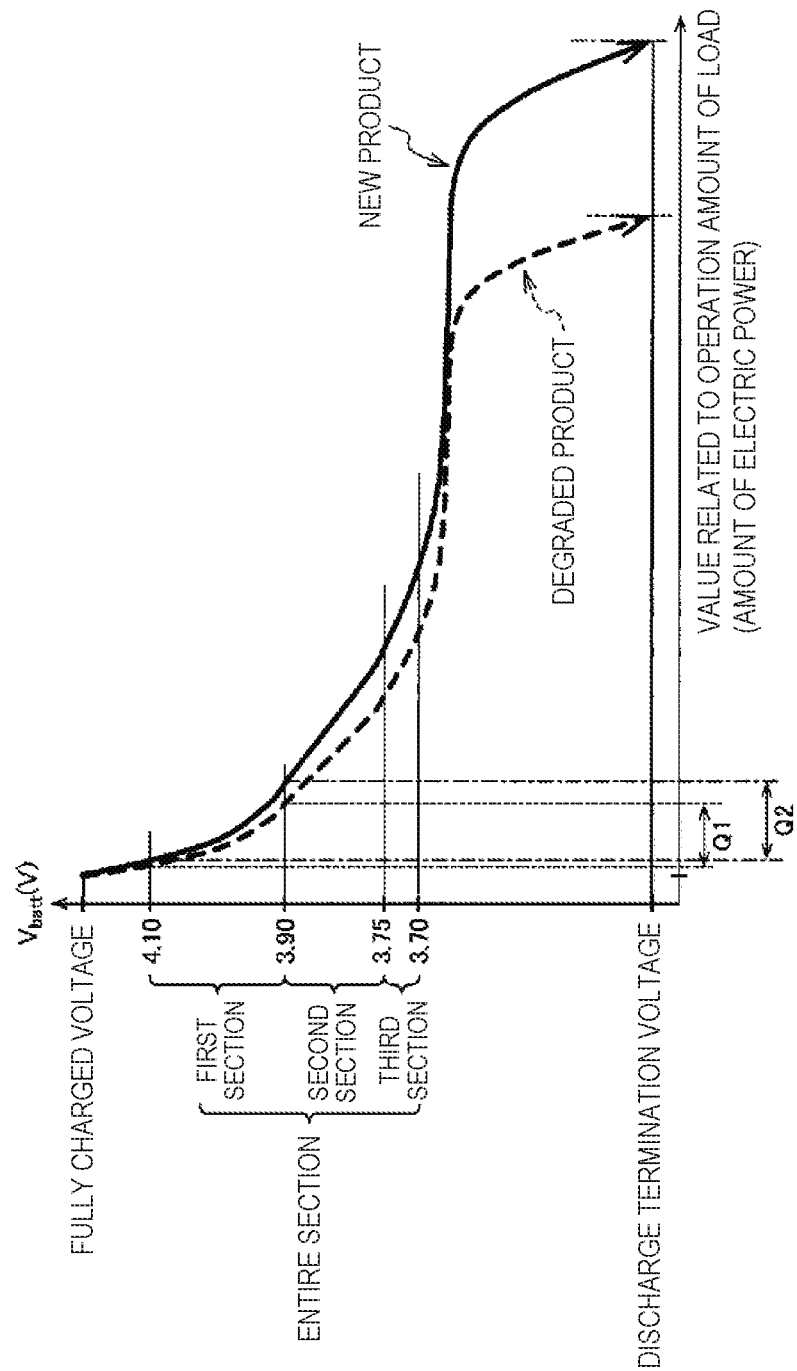
FIG. 10 is a graph for explaining a predetermined voltage range for the first diagnostic function.

FIG. 9 illustrates an example of a flowchart of the first diagnostic function. The first diagnostic function is processing for estimating or detecting at least one of degradation and failure of the power supply 10 based on the value related to the operation amount of the load 121R operated in a period in which the voltage value of the power supply 10 is in a predetermined voltage range. FIG. 10 is a graph for explaining the predetermined voltage range for the first diagnostic function.

Specifically, the control unit 50 acquires a voltage ($V_{batt}$) of the power supply 10 (step S200). The voltage ($V_{batt}$) of the power supply 10 can be acquired using the voltage sensor 150. The voltage of the power supply 10 may be an open circuit voltage (OCV) acquired in a state in which the load 121R is not electrically connected to the power supply 10, or may be a closed circuit voltage (CCV) acquired in a state in which the load 121R is electrically connected to the power supply 10. Note that it is preferable that the voltage of the power supply 10 is defined by the open circuit voltage (OCV) rather than by the closed circuit voltage (CCV) to eliminate the influences of changes in internal resistance and temperature due to voltage drop and discharge accompanying electrical connection of the load 121R. The open circuit voltage (OCV) is obtained by acquiring the voltage of the power supply 10 in a state in which the switch 140 is turned off. Note that the open circuit voltage (OCV) may be estimated from the closed circuit voltage (CCV) by known various methods instead of acquiring the open circuit voltage (OCV) using the voltage sensor 150.

Next, the control unit 50 determines whether the acquired voltage of the power supply 10 is equal to or lower than an upper limit value of the predetermined voltage range (step S202). When the voltage of the power supply 10 is higher than the upper limit value of the predetermined voltage range, the process ends without estimating or detecting degradation and failure of the power supply.

When the voltage of the power supply 10 is equal to or smaller than the upper limit value of the predetermined voltage range, the control unit 50 determines whether the voltage of the power supply acquired one time earlier, i.e., in the previous puff operation is equal to or lower than the upper limit value of the above-described predetermined voltage range (step S204). When the voltage value of the power supply 10 acquired one time earlier, i.e., in the previous puff operation is higher than the upper limit value of the above-described predetermined voltage range, the control unit 50 can determine that the voltage value of the power supply 10 becomes equal to or lower than the upper limit value of the above-described predetermined voltage range by the latest puff operation for the first time. In this case, an accumulation counter (ICo) for counting an accumulated value of values related to the operation amount of the load 121 is set to "0" (step S206). When the accumulation counter (ICo) is set to "0," the process proceeds to the following step S208.

When the voltage value of the power supply acquired one time earlier, i.e., in the previous puff operation is equal to or lower than the upper limit value of the above-described predetermined voltage range (step S204), or the accumulation counter (ICo) is set to "0" (step S206), the control unit 50 determines whether the voltage of the power supply 10 is lower than a lower limit value of the predetermined voltage range (step S208).

When the voltage of the power supply 10 is equal to or higher than the lower limit value of the predetermined voltage range, an integral value "ICo=ICo+Co" of the values related to the operation amount of the load 121R is derived (step S210). Here, "Co" is a value accumulatively obtained in step S112 illustrated in FIG. 7. Then, the process ends without estimating or detecting degradation or failure of the power supply 10.

When this process ends, the control unit 50 waits until acquiring an operation request signal to the load 121R again (step S102 in FIG. 7). When the control unit 50 acquires the operation request signal to the load 121R again, the control unit 50 derives a value (Co) related to the operation amount of the load 121R in one puff operation, and starts the first diagnostic function S114 again.

When the voltage of the power supply 10 is within the predetermined voltage range in the first diagnostic function, the control unit 50 accumulates the values related to the operation amount of the load 121R (step S210). Thereby, the control unit 50 can acquire a value related to the operation amount of the load 121R operated in a period in which the voltage value of the power supply 10 is in a predetermined voltage range.

In step S208, when the voltage of the power supply 10 is lower than the lower limit value of the predetermined voltage range, the control unit 50 determined whether a value related to the operation amount of the load 121R operated in a period in which the acquired voltage value of the power supply 10 is in a predetermined voltage range, i.e., the above-described integral value of ICo is larger than a predetermined threshold (step S220). When the above-described integral value of ICo is larger than the predetermined threshold, the control unit 50 determines that the power supply 10 is normal, and the processing of the first diagnostic function ends.

When the above-described integral value of ICo is equal to or smaller than the predetermined threshold, the control unit 50 determines that the power supply 10 is degraded or fails (step S220), and the control unit 50 notifies the user of abnormality through the notification part 40 (step S224). The notification part 40 can notify the user of degradation or failure of the power supply 10 by predetermined light, sound or vibration. In addition, when the control unit 50 determines that the power supply 10 is degraded or fails, the control unit 50 may perform control to disable the power supply to the load 121R as necessary. Note that in the present embodiment, when the voltage of the power supply 10 is determined to be lower than the lower limit value of the predetermined voltage range (step S208), the value Co related to the operation amount of the load 121R is not added to the integral value ICo of the values related to the operation amount of the load 121R. In other words, when step S208 is determined to be affirmative, step S210 is not performed. Alternatively, when the voltage of the power supply 10 is determined to be lower than the lower limit value of the predetermined voltage range (step S208), the value Co related to the operation amount of the load 121R may be added to the integral value ICo of the values related to the operation amount of the load 121R. In other words, even when step S208 is determined to be affirmative, the same step as step S210 may be performed. In this case, the same step as step S210 can be performed before step S220.

As shown in FIG. 10, when the power supply 10 is degraded, the voltage of the power supply 10 rapidly decreases with an increase in the value related to the operation amount of the load, for example, the amount of electric power to the load 121 or the operation time of the load 121. Therefore, the value related to the operation amount of the load 121R operated in a period in which the voltage value of the power supply 10 is in a predetermined voltage range decreases with the degradation of the power supply. This is shown by the relationship "Q1<Q2" in FIG.

10. In addition, "Q1" in FIG. 10 is a value related to the operation amount of the load 121R operated in a period in which the voltage value of the power supply 10 is in a predetermined voltage range when the power supply 10 is a degraded product. On the other hand, "Q2" in FIG. 10 is a value related to the operation amount of the load 121R operated in a period in which the voltage value of the power supply 10 is in a predetermined voltage range when the power supply 10 is new. Therefore, as described above, the control unit 50 can estimate or detect the degradation of the power supply 10 based on the value related to the operation amount of the load 121R operated in a period in which the voltage value of the power supply 10 is in a predetermined voltage range. Note that when the power supply 10 fails, the voltage of the power supply 10 rapidly decreases with an increase in the value related to the operation amount of the load, for example, the amount of electric power to the load 121R or the operation time of the load 121, as in the case where the power supply 10 is degraded. Accordingly, the control unit 50 can estimate or detect the failure of the power supply 10 based on the value related to the operation amount of the load 121R operated in a period in which the voltage value of the power supply 10 is in a predetermined voltage range. That is, the control unit 50 can estimate or detect at least one of degradation and failure of the power supply 10 based on the value related to the operation amount of the load 121R operated in a period in which the voltage value of the power supply 10 is in a predetermined voltage range.

The predetermined threshold used in step S220 may be determined by experiment in advance according to the type of the power supply 10. The predetermined threshold is set to be lower than a value related to the operation amount of the load 121R by which the new power supply 10 can operate in the predetermined voltage range.

The value related to the operation amount of the load 121R may be the amount of electric power supplied to the load 121R, the operation time of the load 121R, the consumption amount of the inhalation component source, or the like, as described above.

Here, as described above, when the pulse width modulation (PWM) control of electric power supplied to the load 121R is performed based on the voltage of the power supply 10 acquired by the voltmeter 150, a value related to the operation amount of the load 121R is, more preferably, the operation time of the load 121R. In this case, the operation time of the load 121R is a time period required for one puff operation, i.e., a time period from the acquisition of the operation request signal to the load 121R until the end timing of the power supply to the load 121R is detected. Since the amount of electric power supplied to the load 121R per unit time is equalized by the pulse width modulation (PWM) control, the operating time of the load 121R is proportional to the total amount of electric power supplied to the load 121R in a predetermined voltage range. Therefore, when the pulse width modulation (PWM) control of the electric power supplied to the load 121R is performed, the value related to the operation amount of the load 121R is defined by the operation time of the load 121R, thereby high accurate diagnosis of the power supply 10 can be performed with relatively simple control.

Instead of the example described above, the value related to the operation amount of the load 121R may be the number of operations of the load 121R operated in a predetermined voltage range. In this case, steps S110 and S112 are unnecessary in the flowchart of FIG. 7. Then, in the flowchart of FIG. 9, the number of times that the voltage of the power supply 10 has entered the predetermined voltage range may be counted. Specifically, "ICo=ICo+Co" may be replaced with "ICo=ICo+1" in step S210.

Furthermore, instead of the example described above, the value related to the operation amount of the load 121R may be the number of replacement times of the replaceable cartridge containing an inhalation component source, for example, the flavor unit 130. In the inhalation component generation device 100 in which the cartridge needs to be replaced a plurality of times before the charge of the power supply 10 is consumed, the number of replacement times of the cartridge can also be used as a value related to the operation amount of the load 121R.

When a temperature of the power supply 10 is lower than a first temperature threshold, the control unit 50 may be configured to be capable of changing or correcting an algorithm for estimating or detecting at least one of degradation and failure of the power supply 10, i.e., an algorithm for performing the first diagnostic function illustrated in FIG. 9. Specifically, it is preferable that the control unit 50 corrects the predetermined threshold in step S220 to be smaller, and performs the comparison in step S220 based on the corrected threshold. The first temperature threshold may be set, for example, in the range of 1 to 5° C.

It is known that when the temperature of the power supply 10 is low, the internal resistance (impedance) of the power supply 10 increases. As a result, even when the power supply 10 is not degraded, the operation amount of the load 121R operated in a period in which the voltage value of the power supply 10 is in a predetermined voltage range is reduced. Therefore, when the temperature of the power supply 10 is low, the predetermined threshold in step S220 is corrected to be smaller to alleviate the influence of the temperature and to suppress deterioration in detection accuracy of degradation or failure of the power supply 10.

Furthermore, when the temperature of the power supply 10 is lower than a second temperature threshold, the control unit 50 may be configured not to estimate or detect at least one of degradation and failure of the power supply 10. That is, when the temperature of the power supply 10 is lower than the second temperature threshold, the control unit 50 does not necessarily perform the first diagnostic function illustrated in FIG. 9. Here, the second temperature threshold may be smaller than the first temperature threshold. The second temperature threshold may be set, for example, in the range of −1 to 1° C.

Furthermore, when the temperature of the power supply 10 is lower than a third temperature threshold, the control unit 50 may heat the power supply 10 by the control of the heater 70. When the temperature of the power supply 10 is low, increasing the temperature of the power supply 10 can suppress deterioration in detection accuracy of degradation or failure of the power supply 10. The third temperature threshold may be set, for example, in the range of −1 to 1° C.

(Predetermined Voltage Range for First Diagnostic Function)

The predetermined voltage range used in the first diagnostic function will be further described with reference to FIG. 10. The predetermined voltage range may be a predetermined section (voltage range) between the discharge termination voltage and the fully charged voltage. Therefore, the first diagnostic function is not performed when the voltage value of the power supply 10 is lower than the discharge termination voltage.

It is preferable that the predetermined voltage range is set to a range excluding a plateau range in which a change in voltage value of the power supply 10 with respect to a change in the charged amount or state of charge of the power supply 10 is smaller than other voltage ranges. The plateau range is defined, for example, by a voltage range in which the amount of change in the voltage of the power supply 10 with respect to the change in the state of charge (SOC) is 0.01 to 0.005 (V/%) or less.

Since the plateau range has a large storage capacity in a relatively small voltage range, the value related to the operation of the load 121R may fluctuate significantly in the relatively small voltage range. Therefore, the possibility of false detection in the first diagnostic function described above is increased. Therefore, it is preferable that the predetermined voltage range is set to a range excluding the plateau range.

The plateau range in which the predetermined voltage range is not set may be defined by a range including both of a plateau range in which a change in the voltage value of the power supply 10 in a new state with respect to a change in the charged amount or state of charge of the power supply 10 is smaller than other voltage ranges and a plateau range in which a change in the voltage value of the power supply 10 in a degraded state with respect to a change in the charged amount or state of charge of the power supply 10 is smaller than other voltage ranges. As a result, the possibility of causing false detection can be reduced for both of the power supply 10 in the new state and the power supply 10 in the degraded state.

Also, the first diagnostic function may be performed in a plurality of predetermined voltage ranges. It is preferable that the plurality of predefined voltage ranges do not overlap one another. The control unit 50 can perform the first diagnostic function in the same flow as the flowchart illustrated in FIG. 9 in each predetermined voltage range.

In the example illustrated in FIG. 10, three predetermined voltage ranges (a first section, a second section and a third section) are set. In an example, the upper limit value of the first section may be 4.1 V and the lower limit value of the first section may be 3.9 V. The upper limit value of the second section may be 3.9 V, and the lower limit value of the second section may be 3.75 V. The upper limit value of the third section may be 3.75 V, and the lower limit value of the third section may be 3.7 V.

The control unit 50 may perform the comparison in step S220 in each of the plurality of predetermined voltage ranges, and determine that the power supply 10 has been degraded or has failed when the value related to the operation amount of the load 121R in at least one of the plurality of predetermined voltage ranges is equal to or smaller than the above-described predetermined threshold (see step S220).

It is preferable that the plurality of predetermined voltage ranges are set to be narrower as the voltage range in which the change in the voltage value of the power supply 10 with respect to the change in the charged amount or state of charge of the power supply 10 is smaller. As a result, the value related to the operation amount of the load 121R operating in each predetermined voltage range is equalized, so that the accuracy of the first diagnostic function performed in each predetermined voltage range is equalized.

Furthermore, the control unit 50 may be configured to be capable of estimating or detecting at least one of degradation and failure of the power supply 10 based on the value related to the operation amount of the load 121R operated in a period in which the voltage value of the power supply 10 is in a specific voltage range even in the specific voltage range covering one or more of the plurality of predetermined voltage ranges. Specifically, the control unit 50 may set, for example, a voltage range including at least two, preferably three of the first, second and third sections shown in FIG. 10 as a specific voltage range, and perform the diagnostic function illustrated in FIG. 9.

When the diagnostic function illustrated in FIG. 9 is performed in the specific voltage range covering two or more predetermined voltage ranges adjacent to each other among the plurality of predetermined voltage ranges, it is preferable that the predetermined threshold used in step S220 is smaller than the total sum of the predetermined thresholds used in step S220 of the flowchart illustrated in FIG. 9 that is performed in the respective predetermined voltage ranges. For example, the predetermined threshold used in step S220 when the flowchart illustrated in FIG. 9 is performed in the entire section including the first section, the second section, and the third section may be smaller than the total sum of the predetermined thresholds used in step S220 when the flowcharts illustrated in FIG. 9 are separately performed in the first section, the second section and the third section, respectively. As a result, at least one of degradation and failure of the power supply 10 may be estimated or detected in the entire section in some cases, even when at least one of degradation and failure of the power supply 10 cannot be estimated or detected in each of the first section, the second section, and the third section depending on the state of the power supply 10 and how to use the inhalation component generation device 100. Therefore, the accuracy of estimating or detecting at least one of degradation and failure of the power supply 10 can be improved.

(Irregular Processing of First Diagnostic Function)

When charging the power supply 10 causes the power supply 10 to be charged to a value larger than the lower limit of the predetermined voltage range and smaller than the upper limit of the predetermined voltage range, and the power supply 10 is typically not charged to the fully charged voltage, the value related to the operation amount of the load 121R operated in the entire predetermined voltage range cannot be acquired, resulting that the first diagnostic function illustrated in FIG. 9 described above does not function properly in some cases.

In addition, when a long period of time has elapsed since vaporization or atomization of the inhalation component source by the load 121R, the power supply 10 may be naturally discharged by a dark current or the like, and the voltage of the power supply 10 may naturally decrease. In such a case, the voltage range that contributes to the vaporization or atomization of the inhalation component source does not become 100% with respect to the predetermined voltage range described above, and may be equal to or less than a predetermined ratio or width. For example, it is assumed that the voltage of the power supply 10 decreases from 3.9 V to 3.8 V by vaporization or atomization of the inhalation component source, and then the voltage of the power supply 10 becomes 3.65 V after prolonged neglect. In this case, the voltage range that contributes to the vaporization or atomization of the inhalation component source is about 40% with respect to the predetermined voltage range (the second section in FIG. 10). As described above, when the voltage of the power supply 10 significantly decreases regardless of the vaporization or atomization of the inhalation component source, the first diagnostic function illustrated in FIG. 9 described above does not function properly in some cases.

Such prolonged neglect can be detected based on an elapsed time obtained by measuring the time period having elapsed since vaporization or atomization of the inhalation component source by the load 121R. That is, the control unit 50 may start a timer that counts the elapsed time at step S108 of FIG. 7. Instead of this, the prolonged neglect can also be detected based on the voltage change of the power supply 10 after vaporization or atomization of the inhalation component source by the load 121R. In this case, the control unit 50 may acquire the difference between the present voltage of the power supply 10 and the voltage of the power supply 10 previously acquired at the step S200 of FIG. 9. When the difference in voltage exceeds a predetermined value, the control unit 50 can determine that the prolonged neglect has occurred.

Therefore, as described above, when a situation occurs such that the first diagnostic function does not function properly, it is preferable to correct the algorithm of the first diagnostic function or not to perform the first diagnostic function.

For example, it is preferable that the control unit 50 does not perform the determination of the degradation or failure of the power supply 10 in the predetermined voltage range when the range contributing to the vaporization or atomization of the inhalation component source in the predetermined voltage range is equal to or less than the predetermined ratio or width. As a result, the control unit 50 can prevent false detection in the first diagnostic function when a value related to the operation amount of the load 121R operated over the entire predetermined voltage range cannot be acquired due to incomplete charging, natural discharge, and the like.

Instead of this, the control unit 50 may correct to reduce the predetermined threshold in step S220 illustrated in FIG. 9 when the range contributing to the vaporization or atomization of the inhalation component source in the predetermined voltage range is equal to or less than the predetermined ratio or width. For example, the first diagnostic function can be performed while suppressing false detection of the first diagnostic function by correcting to reduce the predetermined threshold according to the range contributing to the vaporization or atomization of the inhalation component source in the predetermined voltage range.

Furthermore, as described above, when the first diagnostic function is performed in a plurality of predetermined voltage ranges, the control unit 50 does not necessarily perform the determination of the vaporization or atomization of the power supply in the irregular range in which the range contributing to the vaporization or atomization of the inhalation component source among the plurality of predetermined voltage ranges is equal to or less than the predetermined ratio or width. That is, in each of the predetermined voltage ranges (for example, the first section, the second section, and the third section), the control unit 50 does not perform the determination of the degradation or failure of the power supply in the section (irregular range) in which a value related to the operation amount of the load 121R cannot be sufficiently acquired due to incomplete charging, natural discharge, and the like.

Even in such a case, the control unit 50 may estimate or detect at least one of degradation and failure of the power supply 10 based on the value related to the operation amount of the load 121R operated in a period in which the voltage value of the power supply 10 is in a specific voltage range in the specific voltage range covering one or more of the plurality of predetermined voltage ranges. In this case, it is preferable that the specific voltage range covering one or more predetermined voltage ranges is set excluding an irregular range.

For example, in the example shown in FIG. 10, when the power supply 10 is charged until the voltage of the power supply 10 becomes 4.05 V, the first diagnostic function is not necessarily performed in the first section. In this case, at least one of degradation and failure of the power supply 10 may be estimated or detected based on the value related to the operation amount of the load 121R operated in the voltage range of the combined section (3.7 V to 3.9 V) of the second section and the third section.

In this case, the predetermined threshold used in step S220 in the case of performing the first diagnostic function based on the value related to the operation amount of the load 121R operated in the voltage range of the combined section of the first section and the second section may be configured by subtracting a value equal to or smaller than the predetermined threshold used in step S220 in the case of performing the first diagnostic function based on the value related to the operation amount of the load 121R operated in the voltage range of the third section from the predetermined threshold (specific threshold) used in step S220 in the case of performing the first diagnostic function based on the value related to the operation amount of the load 121R operated in the voltage range of the entire combined section of the first section, the second section and the third section.

Furthermore, as described above, when there is an irregular range in a plurality of predetermined voltage ranges, and the first diagnostic function is performed in a wider range including the irregular range, for example, the entire section (the first section, the second section, and the third section), the predetermined threshold used in step S220 may be corrected to be reduced.

The control unit 50 may correct at least one of the lower limit value of the predetermined voltage range and the predetermined threshold based on the voltage of the power supply 10 contributing to vaporization or atomization of the inhalation component source after prolonged neglect in the predetermined voltage range. As an example, the control unit 50 may correct to reduce the lower limit value of the predetermined voltage range (to approach 0 V) to perform the first diagnosis function in the predetermined voltage range without correcting the predetermined threshold. As another example, the control unit 50 may perform the first diagnostic function in the predetermined voltage range by correcting to reduce the predetermined threshold without correcting the lower limit value of the predetermined voltage range. As further another example, the control unit 50 may correct both of the lower limit value of the predetermined voltage range and the predetermined threshold to perform the first diagnostic function in the predetermined voltage range.

Note that the control unit 50 may set a new predetermined voltage range and the corresponding predetermined threshold in step S220 illustrated in FIG. 9 based on the voltage of the power supply 10 contributing to the vaporization or atomization of the inhalation component source after prolonged neglect in the predetermined voltage range and the value related to the operation amount of the load 121R operated until the voltage of the power supply 10 is dropped from the voltage to the lower limit value of the predetermined voltage range. This newly set predetermined voltage range is used in the first diagnostic function at and after the next charging.

The control unit 50 may correct at least one of the lower limit value of the predetermined voltage range and the predetermined threshold based on the voltage of the power supply 10 contributing to vaporization or atomization of the inhalation component source after prolonged neglect in the predetermined voltage range. As an example, the control unit 50 may correct to reduce the lower limit value of the predetermined voltage range (to approach 0 V) to perform the first diagnosis function in the predetermined voltage range without correcting the predetermined threshold. As another example, the control unit 50 may perform the first diagnostic function in the predetermined voltage range by correcting to reduce the predetermined threshold without correcting the lower limit value of the predetermined voltage range. As further another example, the control unit 50 may correct both of the lower limit value of the predetermined voltage range and the predetermined threshold to perform the first diagnostic function in the predetermined voltage range.

In addition, the control unit 50 may continue to monitor the voltage of the power supply 10 even when the inhalation component generation device 100 is not used, for example, while the load 121R is not operating. In this case, the control unit 50 may perform the first diagnostic function while correcting the predetermined threshold in step S220 illustrated in FIG. 9 as described above even when the voltage of the power supply 10 falls below the upper limit value of the predetermined voltage range not contributing to the vaporization or atomization of the inhalation component source such as natural discharge.

Instead of this, the control unit 50 may acquire an integral value obtained by integrating the time in which the voltage of the power supply 10 has dropped without contributing to the vaporization or atomization of the inhalation component source. If this integral value is converted into a value related to the operation amount of the load 121R based on a predetermined relationship, the first diagnostic function can be performed without correcting the predetermined threshold in step S220 illustrated in FIG. 9 as described above. That is, the control unit 50 may integrate, as an integral value, the time in which the voltage of the power supply 10 has dropped without contributing to the vaporization or atomization of the inhalation component source in the predetermined range, and add a value obtained by correcting the integral value based on a predetermined relationship to the value related to the operation amount of the load. As an example, the integral value may be corrected to be reduced based on the ratio between a current value or power consumption per unit time when the voltage of the power supply 10 drops without contributing to the vaporization or atomization of the inhalation component source and a current value or power consumption per unit time when the voltage of the power supply 10 drops while contributing to the vaporization or atomization of the inhalation component source, and may be converted into a value related to the operation amount of the load 121R. Note that the current value or power consumption per unit time when the voltage of the power supply 10 drops without contributing to the vaporization or atomization of the inhalation component source and the current value or power consumption per unit time when the voltage of the power supply 10 drops while contributing to the vaporization or atomization of the inhalation component source may be actually measured using the voltage sensor 150, the current sensor 160, and the like. Alternatively, these values may be stored in advance in a memory or the like in the control unit 50, and the control unit 51 may read these values as necessary. Note that instead of these values, the ratio between the current value or power consumption per unit time when the voltage of the power supply 10 drops without contributing to the vaporization or atomization of the inhalation component source and the current value or power consumption per unit time when the voltage of the power supply 10 drops while contributing to the vaporization or atomization of the inhalation component source may be directly stored in the memory.

(Charge Control by Processor of Charger)

Figure 11:
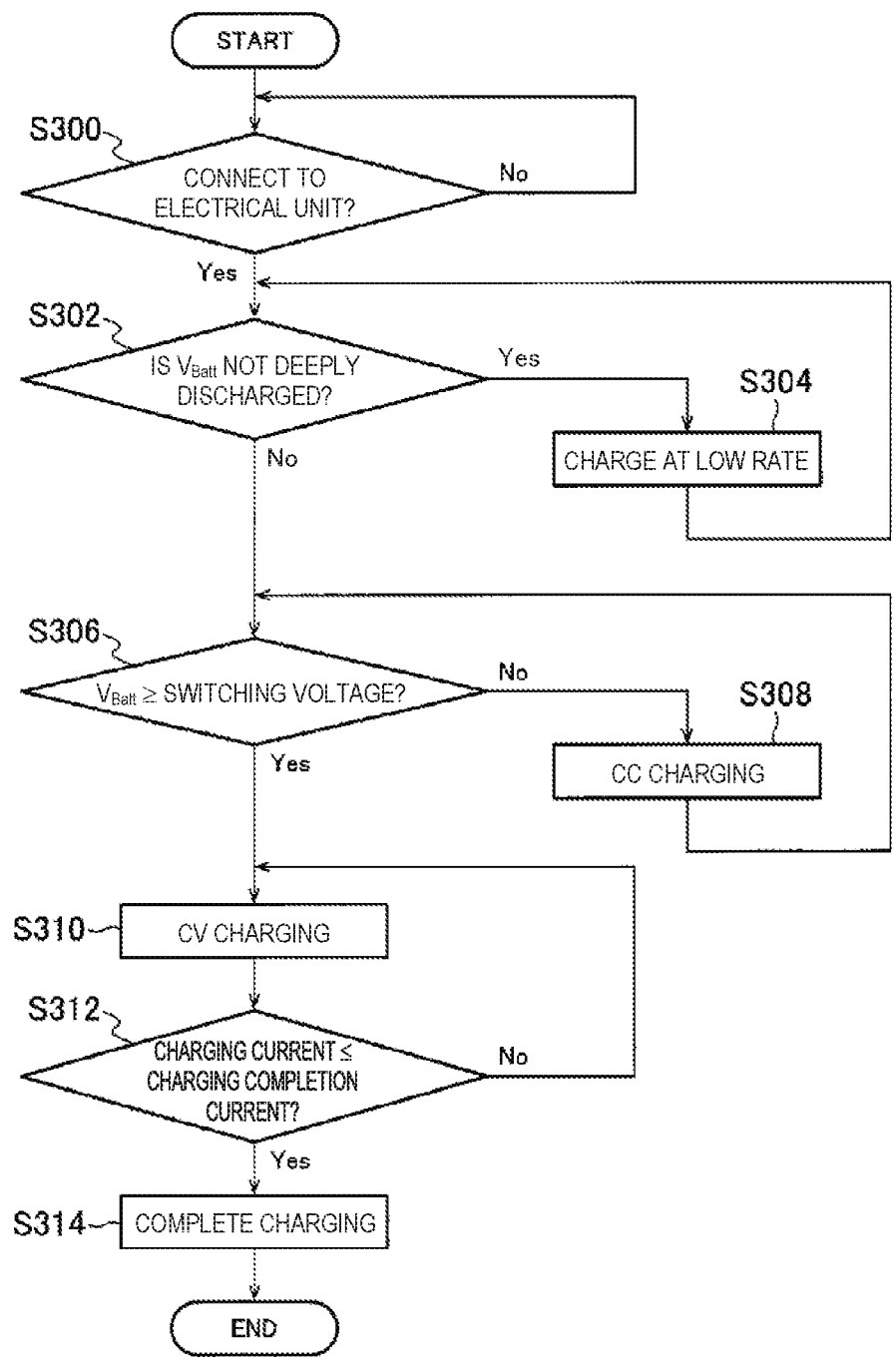
FIG. 11 is a flowchart illustrating an example of a control method by a processor of the charger.

FIG. 11 is a flowchart illustrating an example of a control method by a processor of the charger 200. The processor 250 determines whether to be connected to the electrical unit 110 (step S300). The processor 250 waits until the charger 200 is connected to the electrical unit 110.

The connection between the processor 250 and the electrical unit 110 can be detected in a known method. For example, the processor 250 can determine whether to be connected to the electrical unit 110 by detecting a change in voltage between a pair of electrical terminals of the charger 200 using the voltmeter 240.

When the charger 200 is connected to the electrical unit 110, the processor 250 determines whether the power supply 10 is deeply discharged (step S302). Here, deep discharge of the power supply 10 means a state in which the voltage of the power supply 10 is lower than the deep discharge determination voltage lower than the discharge termination voltage. The deep discharge determination voltage may be, for example, in the range of 3.1 V to 3.2 V.

The processor 250 of the charger 200 can estimate the voltage of the power supply 10 by means of the voltmeter 240. The processor 250 can determine whether the power supply 10 is deeply discharged by comparing the estimated value of the voltage of the power supply 10 with the deep discharge determination voltage.

When the processor 250 determines that the power supply 10 is deeply discharged, the processor 250 charges the power supply 10 with low-rate power (step S304). As a result, the power supply 10 can be recovered from the deeply discharged state to a state of a voltage higher than the discharge termination voltage.

When the voltage of the power supply 10 is equal to or higher than the discharge termination voltage, the processor 250 determines whether the voltage of the power supply 10 is equal to or higher than the switching voltage (step S306). The switching voltage is a threshold for dividing into a section of constant current charging (CC charging) and a section of constant voltage charging (CV charging). The switching voltage may be, for example, in the range of 4.0 V to 4.1 V.

When the voltage of the power supply 10 is less than the switching voltage, the processor 250 charges the power supply 10 by a constant current charging method (step S308). When the voltage of the power supply 10 is equal to or higher than the switching voltage, the processor 250 charges the power supply 10 by a constant voltage charging method (step S310). In the constant voltage charging method, charging proceeds and the voltage of the power supply 10 increases, and therefore the charging current decreases.

When charging of the power supply 10 is started by the constant voltage charging method, the processor 250 determines whether the charging current is equal to or smaller than a predetermined charging completion current (step S312). Here, the charging current can be acquired by the ammeter 230 in the charger 200. When the charging current is larger than the predetermined charging completion current, charging of the power supply 10 is continued by the constant voltage charging method.

When the charging current is equal to or smaller than the predetermined charging completion current, the processor 250 determines that the power supply 10 is fully charged, and stops the charging (step S314).

(Control by Control Unit in Charging Mode)

Figure 12:
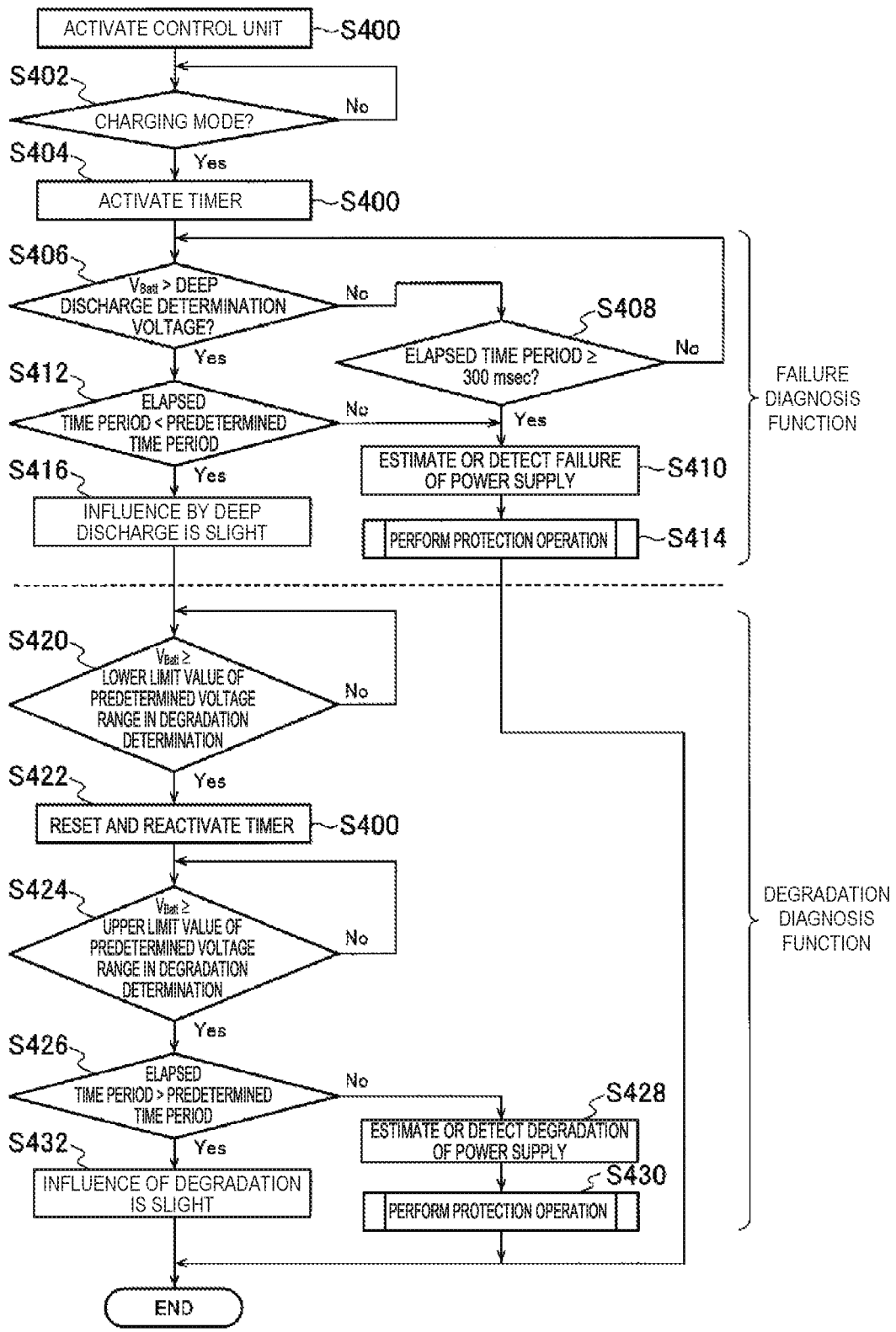
FIG. 12 is a flowchart illustrating an example of a control method of a control unit in a charging mode.
Figure 13:
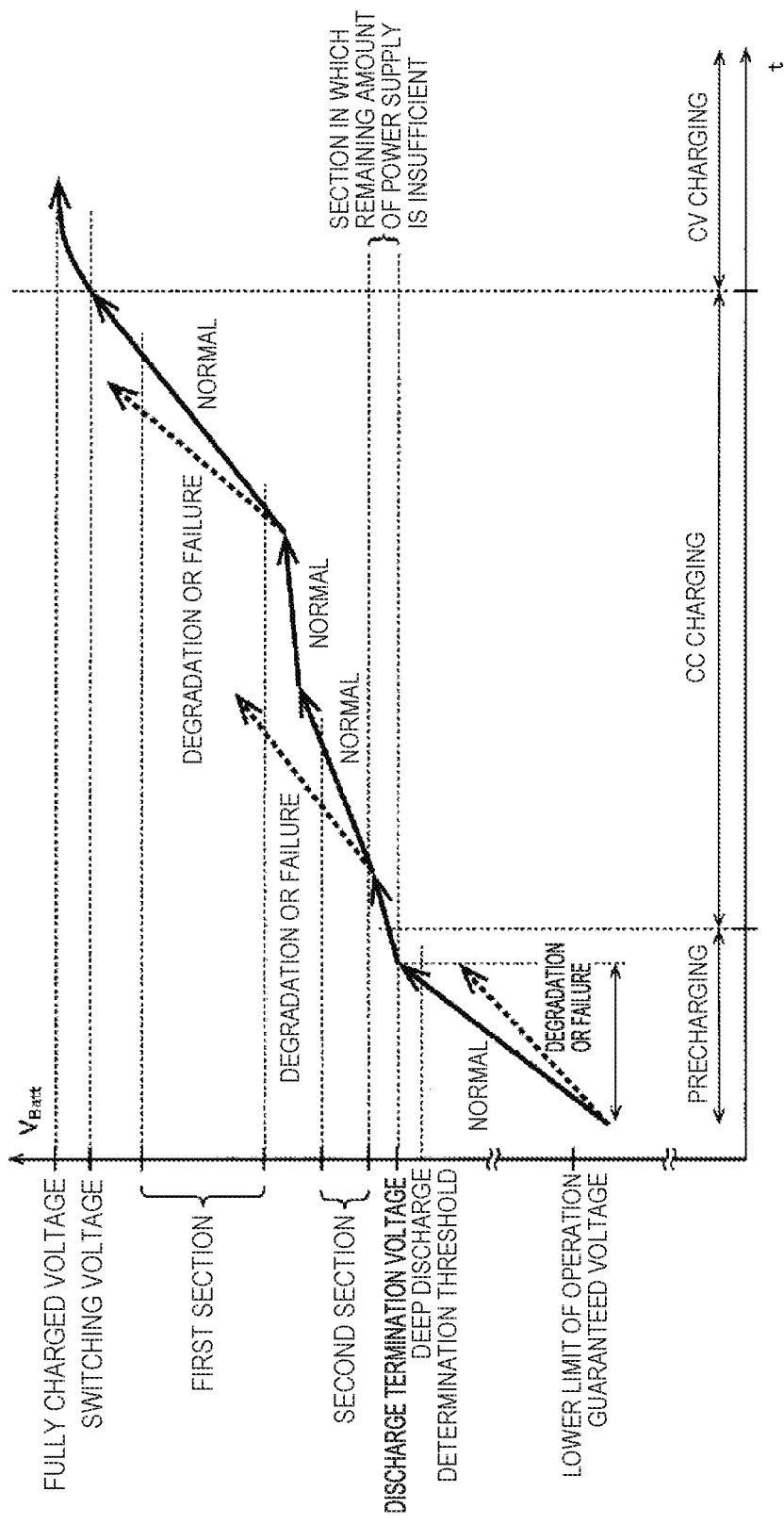
FIG. 13 is a graph for explaining increase in voltage of a normal power supply and a degraded or failed power supply during charging.

FIG. 12 is a flowchart illustrating an example of a control method of the control unit in a charging mode. FIG. 13 is a graph for explaining increase in voltage of a normal power supply and a degraded or failed power supply during charging. The charging mode is a mode in which the power supply 10 can be charged.

The control unit 50 may perform a second diagnostic function that estimates or detects at least one of degradation and failure of the power supply 10 during charging of the power supply 10 by the charger 200. In the present embodiment, the second diagnostic function may include a failure diagnosis function that diagnoses a failure of the power supply 10 and a degradation diagnosis function that diagnoses degradation of the power supply 10. As will be described in detail below, the control unit 50 may be configured to be capable of estimating or detecting at least one of degradation and failure of the power supply 10 based on a time period required for the voltage value of the power supply 10 to reach the upper limit from the lower limit of the predetermined voltage range during charging of the power supply 10. Since the voltage value of the power supply 10 can be acquired by using the voltage sensor 150, the control unit 50 can perform the failure diagnosis function and the degradation diagnosis function described later without communicating with the processor 250 of the charger 200.

Specifically, first, when the control unit 50 is not activated during charging, the control unit 50 is automatically activated (step S400). More specifically, when the voltage of the power supply 10 exceeds a lower limit value of the operation guaranteed voltage of the control unit 50, the control unit 50 is automatically activated. Here, the lower limit value of the operation guaranteed voltage may be in the range of the deep discharge voltage. The lower limit value of the operation guaranteed voltage may be, for example, in the range of 2.0 V to 2.5 V.

The control unit 50 determines whether to be in the charging mode (step S402). The charging mode can be determined by detecting the connection of the charger 200 to the electrical unit 110. The connection of the charger 200 to the electrical unit 110 can be detected by acquiring a change in voltage between the pair of electrical terminals 110t.

When the control unit 50 detects the connection of the charger 200 to the electrical unit 110, a timer is activated, and measures the time from the start of charging or the activation of the control unit (step S404).

Next, the control unit 50 performs the failure diagnosis function of the power supply 10. Specifically, the control unit 50 acquires the voltage ($V_{batt}$) of the power supply 10, and determines whether the voltage ($V_{batt}$) of the power supply 10 is larger than the deep discharge determination voltage (step S406). The voltage ($V_{batt}$) of the power supply 10 can be acquired by using the voltage sensor 150. The deep discharge determination voltage is as described above, and may be, for example, in the range of 3.1 V to 3.2 V (discharge termination voltage). Note that, during the charging of the power supply 10, the control unit 50 periodically acquires the voltage of the power supply 10.

When the electrode structure or the electrolyte of the power supply 10 is irreversibly changed due to deep discharge, the electrochemical reaction during normal charging does not proceed inside the power supply 10 even in charging. Therefore, when the time period in which the voltage ($V_{batt}$) of the power supply 10 is equal to or lower than the deep discharge determination voltage exceeds a predetermined time period, for example, 300 msec, from the activation of the timer, the control unit 50 estimates or detects that the power supply 10 has failed due to deep discharge (steps S408 and S410). In addition, even if the time period required for the voltage value of the power supply 10 to reach the deep discharge determination voltage from the activation of the timer exceeds a predetermined time period, for example, 300 msec, the control unit 50 determines that the power supply 10 has failed due to deep discharge (steps S412 and S410).

When the control unit 50 estimates or detects that the power supply 10 has failed due to deep discharge, the control unit 50 performs a predetermined protection operation (step S414). The protection operation may be, for example, an operation in which the control unit 50 forcibly stops or restricts the charging of the power supply 10. Forced stop or restriction of charging can be achieved by disconnecting the electrical connection between the power supply 10 and the charger 200 in the electrical unit 110. For example, the control unit 50 may turn off at least one of the switch 140 and the stop part 180. The control unit 50 may notify the user of an abnormality through the notification part 40 when the control unit 50 estimates or detects that the power supply 10 has failed due to deep discharge.

As described above, the control unit 50 may perform the failure diagnosis function based on a time period required for the voltage value of the power supply 10 to reach the upper limit from the lower limit of the predetermined voltage range during charging of the power supply 10.

The lower limit of the predetermined voltage range may be, for example, the lower limit value of the operation guaranteed voltage of the control unit 50. In this case, as described above, the control unit 50 performs the failure diagnosis function based on the time period required to reach the deep discharge determination voltage (a predetermined threshold) from the activation of the timer after activation of the control unit 50. Instead of this, the lower limit of the predetermined voltage range may be set to a value lower than the discharge termination voltage of the power supply 10 and larger than the lower limit value of the operation guaranteed voltage of the control unit 50. In this case, the timer may be activated when the voltage of the power supply 10 reaches the lower limit of the predetermined voltage range.

It is preferable that the failure diagnosis function described above is configured to be infeasible when the inhalation component generation device 100 is in a mode other than the charging mode. As a result, when the voltage of the power supply 10 temporarily decreases to deep discharge due to factors such as falling to a very low temperature state in the power supply mode, the failure diagnosis function can be prevented from being erroneously performed.

In addition, the failure diagnosis function described above may be configured to estimate or detect a failure of the power supply when the voltage value of the power supply 10 is lower than the discharge termination voltage of the power supply 10 during charging of the power supply 10.

When the time period required for the voltage value of the power supply 10 to reach the deep discharge determination voltage from the activation of the timer is a predetermined time period, for example, 300 msec or less, it is determined that the influence of deep discharge is small, and charging of the power supply 10 may be continued (step S416). In this case, the control unit 50 may further perform the degradation diagnosis function described below. It is preferable that the control unit 50 is configured not to simultaneously perform the failure diagnosis function and the degradation diagnosis function to prevent hunting of the failure diagnosis function and the degradation diagnosis function.

In the degradation diagnosis function, first, the control unit 50 acquires the voltage value of the power supply 10 during charging, and determines whether the voltage of the power supply is equal to or higher than the lower limit value of the predetermined voltage range (step S420). Here, it is preferable that the upper limit value of the predetermined voltage range used in the failure diagnosis function described above is smaller than the lower limit value of the predetermined voltage range used in the degradation diagnosis function. On the other hand, it is preferable that the predetermined voltage range used in the degradation diagnosis function does not include the discharge termination voltage. By thus setting the predetermined voltage ranges used in each of the failure diagnosis function and the degradation diagnosis function, hunting of the above-described failure diagnosis function and the degradation diagnosis function can be more effectively prevented.

It is more preferable that the control unit 50 is configured to be capable of performing the degradation diagnosis function that estimates or detects degradation of the power supply 10 when the voltage value of the power supply 10 is higher than the discharge termination voltage of the power supply 10 during charging of the power supply 10. Thereby, hunting of the failure diagnosis function and the degradation diagnosis function can be prevented. Note that, to prevent hunting of the failure diagnosis function and the degradation diagnosis function, the control unit 50 may be configured not to perform both of the failure diagnosis function and the degradation diagnosis function when the voltage of the power supply 10 is the discharge termination voltage.

When the voltage of the power supply 10 is equal to or higher than the lower limit value of the predetermined voltage range, the control unit 50 resets the timer and reactivates the timer (step S422). The control unit 50 measures an elapsed time by the timer until the voltage of the power supply 10 becomes equal to or higher than the upper limit value of the predetermined voltage range (step S424).

When the power supply 10 is degraded, the full charging capacity of the power supply 10 tends to decrease although the possible values of the voltage of the power supply 10 such as a fully charged voltage and a discharge termination voltage are not changed. Therefore, the control unit 50 determines whether the elapsed time period required for the voltage of the power supply 10 to reach the upper limit value from the lower limit value of the predetermined voltage range is longer than the predetermined time period (step S426). The control unit 50 estimates or detects that the power supply 10 has been degraded when the voltage value of the power supply 10 has reached the upper limit from the lower limit of the predetermined voltage range within the predetermined time period during charging of the power supply 10 (step S428).

When the control unit 50 estimates or detects that the power supply 10 has been degraded, the control unit 50 performs a predetermined protection operation (step S430). The protection operation may be, for example, an operation in which the control unit 50 forcibly stops or restricts the charging of the power supply 10. Forced stop or restriction of charging can be achieved by disconnecting the electrical connection between the power supply 10 and the charger 200 in the electrical unit 110. For example, the control unit 50 may turn off at least one of the switch 140 and the stop part 180. In addition, the control unit 50 may notify the user of an abnormality through the notification part 40 when the control unit 50 estimates or detects that the power supply 10 has been degraded.

When the voltage value of the power supply 10 does not reach within the predetermined time period from the lower limit to the upper limit of the predetermined voltage range during charging of the power supply 10, the control unit 50 determines that the degradation of the power supply 10 is slight, and charging of the power supply 10 is continued (step S432).

The failure diagnosis function and the degradation diagnosis function may be configured to be performed using the same variable value, and the elapsed time period from the lower limit to the upper limit of the predetermined voltage range in the example described above. In this case, it is preferable that the magnitude relationship between the variable value and the threshold for estimating or detecting that the power supply has failed or has been degraded is reversed between the failure diagnosis function and the degradation diagnosis function. More specifically, the control unit 50 determines that the power supply 10 has failed when the variable value used for the failure diagnosis function, which is the above-mentioned elapsed time period in the above-mentioned example, is larger than the first threshold, for example 300 msec. On the other hand, the control unit 50 determines that the power supply 10 has been degraded when the variable value used for the degradation diagnosis function, which is the above-mentioned elapsed time period in the above-mentioned example, is smaller than the second threshold (predetermined time period). As shown in FIG. 13, in the voltage range equal to or lower than the discharge termination voltage, the voltage of the normal power supply 10 rises during charging earlier than that of the degraded or failed power supply 10. On the other hand, in the voltage range higher than the discharge termination voltage, the voltage of the degraded or failed power supply 10 rises during charging earlier than that of the normal power supply 10. By reversing the magnitude relationship between the variable value and the threshold in the failure diagnostic function and the degradation diagnostic function, it is possible to estimate or detect the degradation or failure of the power supply 10 in both of the failure diagnostic function and the degradation diagnostic function.

When a temperature of the power supply 10 is lower than a fourth temperature threshold, the control unit 50 may be configured to be capable of changing or correcting an algorithm for estimating or detecting at least one of degradation and failure of the power supply 10, i.e., an algorithm for performing the second diagnostic function illustrated in FIG. 12. Specifically, it is preferable that the control unit 50 corrects the predetermined time period in step S412 and/or step S426, and performs the comparison in step S412 and/or step S426 based on the corrected time period threshold. The fourth temperature threshold may be set, for example, in the range of 1 to 5° C.

It is known that when the temperature of the power supply 10 is low, the internal resistance of the power supply 10 is increased. Thereby, even in the power supply 10 which has not been degraded, the time period until the voltage of the power supply 10 reaches the upper limit from the lower limit of the predetermined voltage range changes. Therefore, when the temperature of the power supply 10 is low, the predetermined time period is corrected in step S412 and/or step S426 to thereby alleviate the influence of the temperature and suppress deterioration in detection accuracy of degradation or failure of the power supply 10.

Furthermore, when the temperature of the power supply 10 is lower than a fifth temperature threshold, the control unit 50 may be configured not to estimate or detect at least one of deterioration and failure of the power supply 10. That is, when the temperature of the power supply 10 is lower than the fifth temperature threshold, the control unit 50 does not necessarily perform the failure diagnosis function and/or the degradation diagnosis function illustrated in FIG. 12. Here, the fifth temperature threshold may be smaller than the fourth temperature threshold. The fifth temperature threshold may be set, for example, in the range of −1 to 1° C.

Furthermore, when the temperature of the power supply 10 is lower than a sixth temperature threshold, the control unit 50 may heat the power supply 10 by the control of the heater 70. When the temperature of the power supply 10 is low, increasing the temperature of the power supply 10 can suppress deterioration in detection accuracy of degradation or failure of the power supply 10. The sixth temperature threshold may be set, for example, in the range of −1 to 1° C.

(Predetermined Voltage Range for Degradation Diagnosis Function)

The predetermined voltage range used in the degradation diagnosis function will be further described with reference to FIG. 13. The predetermined voltage range may be a predetermined section (voltage range) between the discharge termination voltage and the fully charged voltage.

It is preferable that the predetermined voltage range is set to a range excluding a plateau range in which a change in voltage value of the power supply 10 with respect to a change in the charged amount or state of charge of the power supply 10 is smaller than other voltage ranges. The plateau range is defined, for example, by a voltage range in which the amount of change in the voltage of the power supply 10 with respect to the change in the state of charge is 0.01 to 0.005 (V/%) or less.

The plateau range is less likely to produce a significant difference between a normal power supply and a degraded power supply due to the small variation of the voltage of the power supply with respect to the elapsed time period of charging. Therefore, the possibility of false detection in the above-mentioned degradation diagnostic function is increased. Accordingly, it is preferable that the predetermined voltage range is set to a range excluding the plateau range.

Furthermore, it is preferable that the predetermined voltage range used in the degradation diagnosis function is set to a range excluding the range in which the constant voltage charging is performed on the power supply 10. The range in which the constant voltage charging is performed corresponds to the end of the charging sequence and thus corresponds to a range in which the fluctuation of the voltage of the power supply with respect to the elapsed time period of charging is small. Therefore, the accuracy of the degradation diagnostic function can be enhanced by setting the predetermined voltage range used in the degradation diagnostic function to a range excluding the range in which the constant voltage charging is performed.

Here, the processor 250 of the charger 200 uses the voltmeter 240 in the charger 200 to estimate the voltage of the power supply 10. Meanwhile, the control unit 50 uses the voltage sensor 150 in the electrical unit 110 to acquire the voltage of the power supply 10. By the way, the voltage of the power supply 10 recognized by the charger 200 is a value obtained by adding a voltage drop in the contact resistance of the connection terminal 110t or the resistance of the lead wire electrically connecting the charger 200 and the power supply 10 to the true value of the voltage of the power supply 10. On the other hand, the voltage of the power supply 10 recognized by the control unit 50 is not affected by at least the voltage drop in the contact resistance of the connection terminal 110t. Therefore, a deviation may occur between the voltage of the power supply 10 recognized by the charger 200 and the voltage of the power supply 10 recognized by the control unit 50. In consideration of this deviation, it is preferable that the voltage range of the power supply 10 that performs the degradation diagnosis function is set to a range lower than the voltage value obtained by subtracting the predetermined value from the switching voltage described above.

Furthermore, it is preferable that the predetermined voltage range used in the degradation diagnosis function is set to a range excluding a range in which the notification part 40 notifies that the remaining amount of the power supply 10 is insufficient. When the predetermined voltage range is set near the discharge termination voltage, the power supply 10 cannot be charged over the entire predetermined voltage range when the power supply 10 is charged before the voltage of the power supply 10 decreases to the discharge termination voltage. Therefore, the above degradation diagnostic function does not function properly in some cases. By setting the predetermined voltage range used in the degradation diagnosis function except for the range in which the remaining amount of the power supply 10 is insufficient, the degradation diagnosis function can be functioned normally even if the voltage of the power supply 10 is charged before the voltage of the power supply 10 decreases to the discharge termination voltage.

Also, the degradation diagnosis function may be performed at a plurality of predetermined voltage ranges. It is preferable that the plurality of predefined voltage ranges do not overlap one another. The control unit 50 can perform the degradation diagnosis function in the same flow as a part of the degradation diagnosis function of the flowchart illustrated in FIG. 12 in each predetermined voltage range. In the example shown in FIG. 13, two predetermined voltage ranges (first and second sections) are set.

(Relationship Between First Diagnostic Function and Second Diagnostic Function)

As described above, the control unit 50 is configured to be capable of performing the first diagnostic function of estimating or detecting at least one of degradation and failure of the power supply 10 during operation of the load 121R, and the second diagnostic function of estimating or detecting at least one of degradation and failure of the power supply 10 during charging of the power supply 10.

Here, it is preferable that the first diagnostic function and the second diagnostic function include different algorithms. Thereby, to estimate or detect at least one of degradation and failure of the power supply 10, an optimal algorithm can be applied according to charging and discharging of the power supply 10.

The first diagnostic function, i.e., the diagnostic function performed during operation of the load 121R may include at least one algorithm for estimating or detecting at least one of degradation and failure of the power supply 10. In the above embodiment, the first diagnostic function includes only one algorithm for estimating or detecting at least one of degradation and failure of the power supply 10.

For example, in a small-sized and portable inhalation component generation device 100 such as an electronic cigarette or a heated tobacco, it is desirable to mount a control unit 50 having a simple control function. When the control unit 50 having such a simple control function is used to control the supply of electric power to the load 121R in the power supply mode, the calculation capability of the control unit 50 is limited in the power supply mode. When the first diagnostic function includes only one algorithm, the control unit 50 can estimate or detect at least one of degradation and failure of the power supply 10 within a range not affecting the other control, for example, the power control to the load 121R.

The second diagnostic function, i.e. the diagnostic function performed during charging of the power supply 10, may include at least one algorithm for estimating or detecting at least one of degradation and failure of the power supply 10. In the above embodiment, the second diagnosis function includes two of the failure diagnosis function and the degradation diagnosis function described above. In addition to the above embodiments, the second diagnostic function may further include one or more other algorithms for estimating or detecting at least one of degradation and failure of the power supply 10.

Preferably, the number of algorithms included in the second diagnostic function is greater than the number of algorithms included in the first diagnostic function. Charging of the power supply 10 is controlled by an external charger 200 separate from the inhalation component generation device 100. Therefore, the control unit 50 has a surplus in calculation capability in the charging mode as compared to the power supply mode. By increasing the number of algorithms included in the second diagnostic function in the charging mode by using the margin of the calculation capability, at least one of degradation and failure of the power supply 10 can be estimated or detected with higher accuracy in the charging mode.

To simplify the structure of the inhalation component generation device 100, the processor 250 of the charger 200 may be configured to be incapable of communicating with the control unit 50 of the electrical unit 110. When the inhalation component generation device 100 is configured as described above, not only the structure can be simplified, but also the control unit 50 does not have to allocate calculation capability for communication with the processor 250 of the charger 200. Therefore, since more calculation capability can be allocated to the second diagnostic function in the charging mode, at least one of degradation and failure of the power supply 10 can be estimated or detected with higher accuracy in the charging mode.

More preferably, the number of simultaneously executable algorithms included in the second diagnostic function is greater than the number of simultaneously executable algorithms included in the first diagnostic function. In the example illustrated in the above embodiment, the failure diagnosis function and the degradation diagnosis function described above may be simultaneously executable. Alternatively, in the charging mode, when the voltage of the power supply 10 drops, a diagnostic function of detecting an internal short circuit of the power supply 10 as a failure may be performed simultaneously with the above-described degradation diagnosis function.

It is preferable that the number of sensors required to perform the second diagnostic function is less than the number of sensors required to perform the first diagnostic function. In the above embodiment, the second diagnostic function can be performed by using the voltage sensor 150 for acquiring the voltage of the power supply 10 and the temperature sensor 170 as needed. On the other hand, the first diagnostic function can be performed by using the voltage sensor 150 for acquiring the voltage of the power supply 10, the request sensor (the inhalation sensor 20 or the push button 30), and the temperature sensor 170 as needed. Note that, the timer for measuring time is not included in a sensor.

It is preferable that the sensors required to perform the second diagnostic function do not include the request sensor (the inhalation sensor 20 or the push button 30). It is unlikely from the normal usability of the inhalation component generation device 100 that the request sensor is operated during charging. In other words, if the sensors required to perform the second diagnostic function include a request sensor that is not originally operated, some inconvenience may occur in the second diagnostic function. Thus, it is preferable that the second diagnostic function performed during charging can be performed without using the request sensor that requests the supply of electric power to the load 121R.

It is preferable that the predetermined voltage range used for the failure diagnosis function and the degradation diagnosis function described above in the second diagnosis function, for example, a combined range of the section from the lower limit of the operation guaranteed voltage to the deep discharge determination threshold, the first section and the second section shown in FIG. 13 is wider than the predetermined voltage range used for the first diagnosis function, for example, a combined range of the first section, the second section, and the third section shown in FIG. 10. Since the range of possible values of the voltage of the power supply 10 in the charging mode is wider than that in the power supply mode, the accuracy of the diagnosis of the degradation or failure of the power supply in the charging mode can be improved by enlarging the predetermined voltage range used in the second diagnostic function.

(Performance of Second Diagnostic Function by Charger)

In the example described above, the control unit 50 of the electrical unit 110 performs the second diagnostic function (the failure diagnostic function and the degradation diagnostic function). Instead of this, the processor 250 of the charger 200 may perform the second diagnostic function that estimates or detects at least one of degradation and failure of the power supply 10 based on the time period required for the voltage value of the power supply 10 to reach the upper limit from the lower limit of the predetermined voltage range during charging of the power supply 10. In this case, the processor 250 of the charger 200 performs an algorithm as a process similar to the process in the flowchart illustrated in FIG. 12.

However, since the processor 250 of the charger 200 performs the second diagnostic function, step S400 in the flowchart illustrated in FIG. 12 is unnecessary. Also, the voltage of the power supply 10 acquired by the processor 250 is estimated by a voltmeter 240 provided in the charger 200. The protection operation (steps S414 and S430) may be an operation in which the processor 250 of the charger 200 stops the charging current. The other processing is the same as when the control unit 50 of the electrical unit 110 performs the second diagnostic function, and thus the description thereof will be omitted. Thus, if the processor of the charger 200 electrically connected to the power supply 10 instead performs at least a part of the second diagnostic function that is be originally performed by the control unit 50, the control unit 50 can perform further another algorithm as the second diagnostic function to thereby improve the accuracy of the diagnosis of the degradation or failure of the power supply in the charging mode.

(Voltage Sensor)

Figure 14:
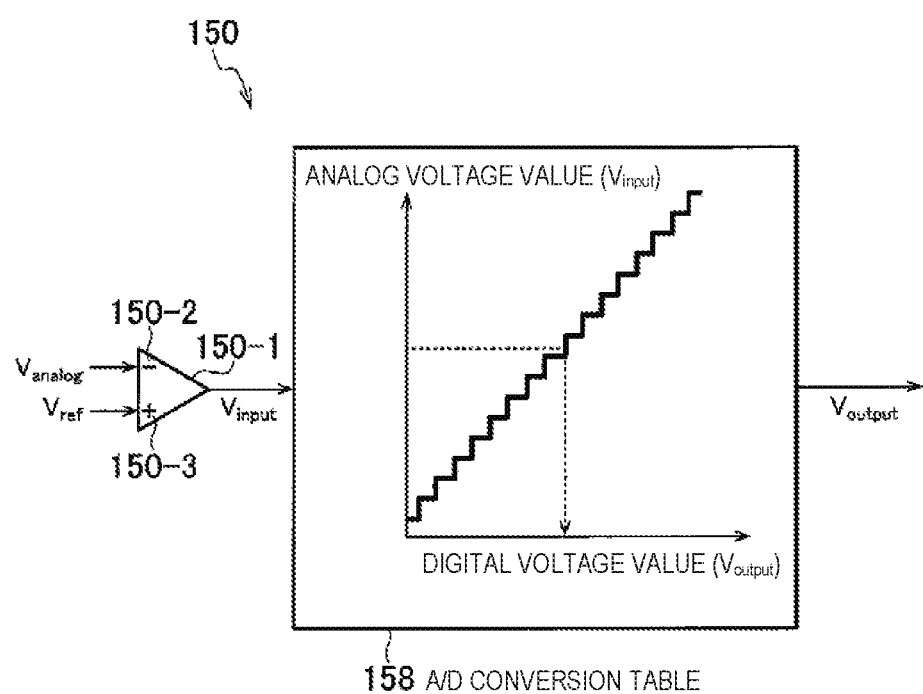
FIG. 14 is a diagram illustrating a block of a voltage sensor.

First, the details of the voltage sensor 150 will be described with reference to FIG. 5 and FIG. 14. The voltage sensor 150 is configured to convert an analog voltage value of the power supply 10 into a digital voltage value using a predetermined correlation, and to output the digital voltage value. Specifically, as illustrated in FIG. 5 and FIG. 14, the voltage sensor 150 may include an A/D converter 154 that converts an analog input value into a digital output value. The A/D converter 154 has a conversion table 158 for converting analog input values into digital output values.

The resolution involved in the conversion to digital voltage values is not limited to a particular resolution, and may be, for example, 0.05 V/bit. In this case, the output value from the voltage sensor 150 is converted every 0.05 V.

Note that the conversion table 158 illustrated in FIG. 14 shows the correlation when the reference voltage ($V_{ref}$) 156 described later is higher than the voltage of the power supply 10, for example, the fully charged voltage of the power supply 10. In this case, in the predetermined correlation 158, a higher analog voltage value is associated with a higher digital voltage value.

A voltage (an analog voltage ($V_{analog}$)) of the power supply 10 is input to an inverting input terminal 150-2 of the operational amplifier 150-1, and a reference voltage ($V_{ref}$) 156 (for example, 5.0 V) which is a constant voltage higher than the voltage (an analog voltage ($V_{analog}$)) of the power supply 10 is input to the other non-inverting input terminal 150-3. The operational amplifier 150-1 inputs the difference of these voltages or the value ($V_{input}$) obtained by amplifying the difference to the A/D converter 154. The A/D converter 154 converts an analog voltage value ($V_{input}$) into a digital voltage value ($V_{output}$) based on the predetermined correlation (conversion table) 158 and outputs it. When the control unit 50 acquires the voltage of the power supply 10 in all the processes described above, the control unit 50 (controller 51) acquires the digital voltage value ($V_{output}$) output from the voltage sensor 150.

Here, it is preferable that when the voltage (analog voltage ($V_{analog}$)) of the power supply 10 is a fully charged voltage, the predetermined correlation (conversion table) 158 is set to output the digital voltage value ($V_{output}$) corresponding to the fully charged voltage, and when the voltage (analog voltage ($V_{analog}$)) of the power supply 10 is a discharge termination voltage, the predetermined correlation (conversion table) 158 is set to output the digital voltage value ($V_{output}$) corresponding to the discharge termination voltage.

However, due to a product error such as a reference voltage, degradation of the power supply 10 or the like, an error may be generated in the digital voltage value ($V_{output}$) to be output. Therefore, it is preferable to properly calibrate the predetermined correlation (conversion table) 158 of the voltage sensor 150.

Figure 15:
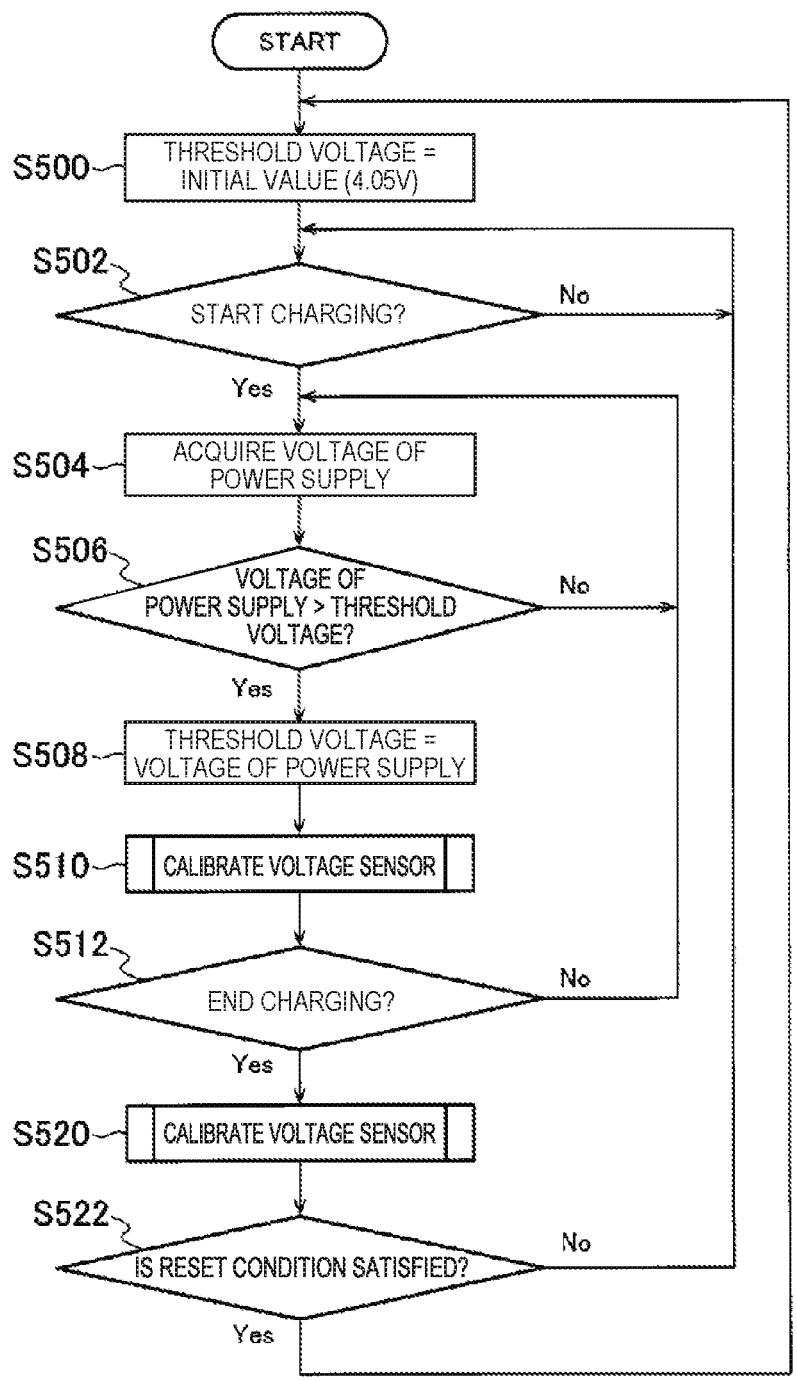
FIG. 15 is a flowchart illustrating processing for calibration of a predetermined correlation of a voltage sensor.

Next, the calibration of the predetermined correlation (conversion table) 158 of the voltage sensor 150 will be described. FIG. 15 is a flowchart illustrating processing for calibration of the predetermined correlation 158 of the voltage sensor 150. The control unit 50 may be configured to be able to calibrate the correlation 158 based on changes in the analog or digital voltage values acquired during charging of the power supply 10.

First, the threshold voltage is set to an initial value (step S500). Here, it is preferable to set the initial value of the threshold voltage to a value smaller than the fully charged voltage of the digital voltage value. For example, the initial value of the threshold voltage is 4.05 V.

The control unit 50 detects the start of charging (step S502). The start of charging may be detected by the connection of the charger 200 to the electrical unit 110. When the charging is started, the control unit 50 acquires the voltage of the power supply 10 every predetermined time (step S504). The acquired voltage of the power supply 10 may be a digital voltage value output from the voltage sensor 150.

Next, the control unit 50 determines whether the acquired voltage of the power supply 10 is higher than the threshold voltage (step S506). When the acquired voltage of the power supply 10 is equal to or lower than the threshold voltage, the voltage of the power supply 10 is acquired again after the elapse of a predetermined time (step S504), and the process returns to step S506.

When the acquired voltage of the power supply 10 is higher than the threshold voltage, the value of the threshold voltage is updated to the acquired voltage value of the power supply 10 (step S508). Then, the control unit 50 calibrates the predetermined correlation 158 of the voltage sensor 150 as necessary (step S510).

Next, the control unit 50 determines whether the charging has been completed (step S512). When the charging has not completed, the voltage of the power supply 10 is acquired again (step S504), and the process returns to step S506. The control unit 50 may calibrate the predetermined correlation 158 of the voltage sensor 150 each time the voltage of the power supply 10 becomes larger than the threshold voltage in the period until the charging ends. In this case, the control unit 50 does not need to perform the process (step S520) of calibrating the predetermined correlation 158 of the voltage sensor 150 after the charging is completed.

Alternatively, the control unit 50 does not necessarily calibrate the predetermined correlation 158 in the period from the charging start to the charging end. That is, the control unit 50 does not need to perform step S510. In this case, the control unit 50 performs a process of calibrating the predetermined correlation 158 of the voltage sensor 150 after the charging is completed (step S520).

As described above, the control unit 50 may perform the process of calibrating the predetermined correlation 158 of the voltage sensor 150 at any one of the timings of step S510 and step S520.

When the predetermined reset condition is satisfied after completion of charging of the power supply 10, the threshold voltage is reset to an initial value, for example, 4.05 V again (step S522). The reset condition may be, for example, that the inhalation component generation device 100 is turned off. This is because a factor causing an error in the digital voltage value ($V_{output}$) output from the voltage sensor 150 due to a product error, degradation of the power supply 10, or the like may vary every time the reset condition such as the inhalation component generation device 100 turning off is satisfied.

In the flowchart illustrated in FIG. 15, it is preferable that the threshold voltage at the time of manufacture or actuation of the inhalation component generation device 100 is set to a value smaller than the fully charged voltage of the power supply 10. Taking into consideration that an error may be generated in the digital output value of the voltage sensor 150, the digital output value of the voltage sensor 150 may stay below the fully charged voltage even if the voltage (analog voltage value) of the power supply 10 reaches the fully charged voltage during the initial charging of the power supply 10. Therefore, by setting the threshold voltage at the time of manufacture or activation of the inhalation component generation device 100 to a value smaller than the fully charged voltage, the predetermined correlation 158 of the voltage sensor 150 can be prevented from becoming uncalibrated during the initial charging of the power supply 10 from the time of manufacture or activation of the inhalation component generation device 100.

More specifically, it is preferable that the threshold voltage at the time of manufacture or activation of the inhalation component generation device 100 is set to be equal to or lower than a value obtained by subtracting the absolute value of the product error from the fully charged voltage (for example, 4.2 V) of the power supply 10 among a plurality of digital voltage values that can be output from the voltage sensor 150. For example, when an error of about ±0.11 V can be generated in the voltage sensor 150, the threshold voltage at the time of manufacture or actuation of the inhalation component generation device 100 may be set to 4.09 V or less.

Furthermore, it is more preferable that the threshold voltage at the time of manufacture or actuation of the inhalation component generation device 100 is set to a maximum value in a range of not higher than a value obtained by subtracting the absolute value of the product error from the fully charged voltage (for example, 4.2 V) of the power supply 10 among a plurality of digital voltage values that can be output from the voltage sensor 150. Thus, when the threshold voltage at the time of manufacture or activation of the inhalation component generation device 100 is set, the predetermined correlation 158 of the voltage sensor 150 can be prevented from becoming uncalibrated during the initial charging of the power supply 10 from the time of manufacture or activation of the inhalation component generation device 100 described above. Furthermore, the voltage sensor 150 can be suppressed from being calibrated more frequently as compared with the case where the threshold voltage at the time of manufacture or activation of the inhalation component generation device 100 is set to a value other than the maximum value in a range of not higher than a value obtained by subtracting the absolute value of the product error from the fully charged voltage (for example, 4.2 V) of the power supply 10 among a plurality of digital voltage values that can be output from the voltage sensor 150.

For example, when the resolution of the digital voltage value is 0.05 V/bit and an error of about ±0.11 V may be generated in the voltage sensor 150, the threshold voltage at the time of manufacture or actuation of the inhalation component generation device 100 may be 4.05 V. This is a voltage value of 4.09 V or less, which is a value obtained by subtracting the absolute value of the product error from the fully charged voltage of the power supply 10. It will be appreciated that the maximum digital voltage value is 4.05 V among the digital voltage values (for example, 3.95 V, 4.00 V, and 4.05 V) that can be output from the voltage sensor 150.

In the flowchart described above, the control unit 50 performs calibration of the predetermined correlation 158 when the digital voltage value obtained during charging of the power supply 10 becomes higher than the threshold voltage. Alternatively, the control unit 50 may perform calibration of the predetermined correlation 158 when the digital voltage value obtained during charging of the power supply 10 reaches a maximum value or a local maximum value.

By recording the history of digital voltage values output from the voltage sensor 150, the control unit 50 can extract the maximum value of the digital voltage values acquired from the start to the end of charging.

Furthermore, by detecting a decrease in digital voltage value output from the voltage sensor 150 during charging, the control unit 50 can extract the local maximum value of the digital voltage values acquired from the start to the end of charging.

Note that the calibration of the predetermined correlation 158 of the voltage sensor 150 does not need to be performed at the timing illustrated in the above-described flowchart, and may be performed at any timing, for example, during charging, after charging, or at the next actuation of the inhalation component generation device 100.

(Predetermined Correlation Calibration)

Next, the calibration of the predetermined correlation 158 of the voltage sensor 150 will be described. The control unit 50 calibrates the correlation 158 so that the digital voltage value higher than the maximum or local maximum value of the digital voltage value acquired during charging of the power supply 10 or the threshold voltage corresponds to the fully charged voltage value of the power supply 10. Here, by charging the power supply 10 to the fully charged voltage even if the correlation 158 is calibrated so that the digital voltage value higher than the threshold voltage corresponds to the fully charged voltage value of the power supply 10, the correlation 158 is finally calibrated so that the maximum or local maximum value of the digital voltage value acquired in at least a part of sections during charging of the power supply 10 corresponds to the fully charged voltage value of the power supply 10.

When the power supply 10 is charged to the full charge, the voltage of the power supply 10 has reached the fully charged voltage. In addition, since the fully charged voltage of the power supply 10 is less likely to be affected by a factor causing the error in the digital voltage value ($V_{output}$) output from the voltage sensor 150 due to a product error such as the reference voltage, degradation of the power supply 10, or the like, the fully charged voltage of the power supply 10 is particularly useful as a reference for calibration. Therefore, when the correlation 158 is calibrated as described above, the voltage sensor 150 outputs a digital voltage value corresponding to the fully charged voltage value when an analog voltage value corresponding to the fully charged voltage is input to the voltage sensor 150. This allows the voltage sensor 150 to be properly calibrated.

Figure 16:
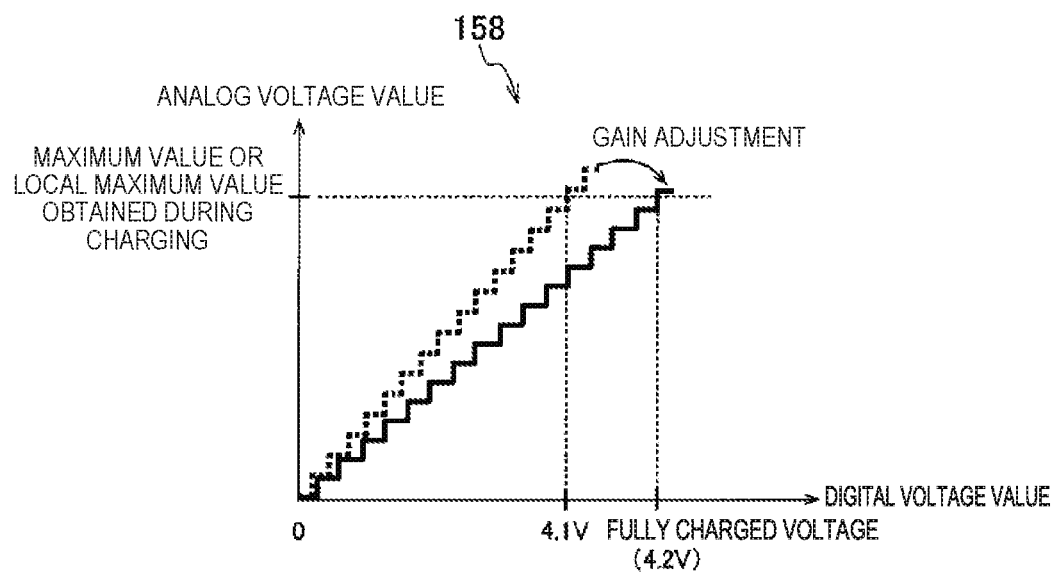
FIG. 16 is a graph showing an example of calibration of the predetermined correlation of the voltage sensor.

FIG. 16 is a graph showing an example of calibration of the predetermined correlation 158 of the voltage sensor 150. As shown in FIG. 16, the predetermined correlation 158 may be calibrated to gain-adjust the correspondence between analog voltage values and digital voltage values. The gain adjustment can be performed, for example, by increasing or decreasing the vertical axis value (analog voltage value) or horizontal axis value (digital voltage value) of the predetermined correlation 158 at a constant rate. That is, in the gain adjustment, the slope of the predetermined correlation 158, more specifically, the slope of the approximate straight line of the predetermined correlation 158 is adjusted.

Figure 17:
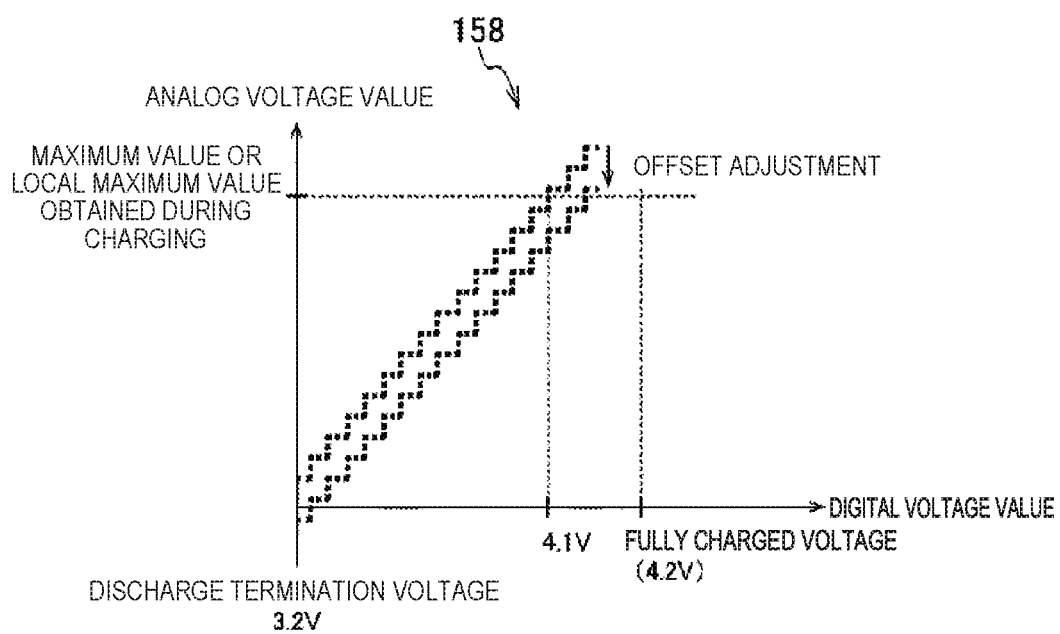
FIG. 17 is a graph showing another example of calibration of the predetermined correlation of the voltage sensor.

FIG. 17 is a graph showing another example of calibration of the predetermined correlation 158 of the voltage sensor 150. As shown in FIG. 17, the predetermined correlation 158 may be calibrated to offset-adjust the correspondence between analog voltage values and digital voltage values. The offset adjustment can be performed, for example, by increasing or decreasing the value (analog voltage value) on the vertical axis of the predetermined correlation 158 by a certain value. The offset adjustment has an advantage of easy adjustment because it merely increases or decreases the intercept of the predetermined correlation 158, specifically, the intercept of the approximate straight line of the predetermined correlation 158 by a certain value.

The relationship between the analog voltage value and the digital voltage value needs to be defined in the range from the discharge termination voltage to the fully charged voltage in both of before and after the offset adjustment. Therefore, it is preferable that the predetermined correlation 158 includes at least one of the correspondence between the digital voltage value lower than the discharge termination voltage of the power supply 10 and the analog voltage value, and the correspondence between the digital voltage value higher than the fully charged voltage of the power supply 10 and the analog voltage value.

The predetermined correlation 158, once calibrated, may be maintained without changing the correlation until the next calibration. Alternatively, the predetermined correlation 158 may return to the initial correlation upon shutdown or subsequent activation of the inhalation component generation device 100. Here, the initial correlation may be a predetermined correlation at the time of manufacture of the inhalation component generation device 100.

At the time of manufacture or activation of the inhalation component generation device 100, it is preferable that the predetermined correlation 158 is calibrated or set so that the analog voltage value less than an analog voltage value corresponding to the fully charged voltage value when the voltage sensor 150 has no error corresponds to the fully charged digital voltage value. That is, at the time of manufacture or activation of the inhalation component generation device 100, the voltage sensor 150 is designed to output a digital voltage value corresponding to the fully charged voltage when a predetermined analog voltage value smaller than the fully charged voltage is input to the voltage sensor 150. For example, at the time of manufacture or activation of the inhalation component generation device 100, the voltage sensor 150 may be designed to output a digital voltage value (4.2 V) corresponding to the fully charged voltage when an analog voltage value of 4.1 V smaller than the fully charged voltage (4.2 V) is input to the voltage sensor 150. Thereby, even if there is a manufacturing error, the voltage sensor 150 is configured to output a digital voltage value that is equal to or higher than an actual analog voltage value at the time of manufacture or actuation of the inhalation component generation device 100.

In this case, in the first charge from the time of manufacture or actuation of the inhalation component generation device 100, the analog voltage value of the actual power supply 10 can be prevented from exceeding the fully charged voltage before the control unit 50 recognizes that the fully charged voltage has been reached. In other words, in the case where the voltage sensor 150 outputs a small digital voltage value due to a manufacturing error or the like with respect to the actual value of the voltage of the power supply 10, the voltage value of the power supply 10 can be prevented from exceeding the fully charged voltage, thereby falling into overcharge, when the voltage sensor 150 outputs a digital voltage value corresponding to the fully charged voltage of the power supply 10. Therefore, if the control unit 50 has a process of forcibly stopping charging when the output voltage value from the voltage sensor 150 exceeds the fully charged voltage, overcharge of the power supply 10 can be prevented.

It is more preferable that the predetermined correlation 158 at the time of manufacture or actuation of the inhalation component generation device 100 is calibrated or set so that the analog voltage value corresponding to a value closest to the value obtained by subtracting the absolute value of the product error from the fully charged voltage of the power supply 10 when the voltage sensor 150 has no error corresponds to the fully charged voltage value among a plurality of digital voltage values that can be output from the voltage sensor 150. As a result, the power supply 10 can be prevented from being overcharged by underestimating the voltage of the power supply 10 due to a product error or the like. Furthermore, in the initial state of the predetermined correlation 158, the difference in numerical value between the analog voltage value and the digital voltage value is increased, and the actual value of the power supply 10 and the digital voltage corresponding thereto can be suppressed from being separated from each other.

(Another Aspect of Predetermined Correlation)

Figure 18:
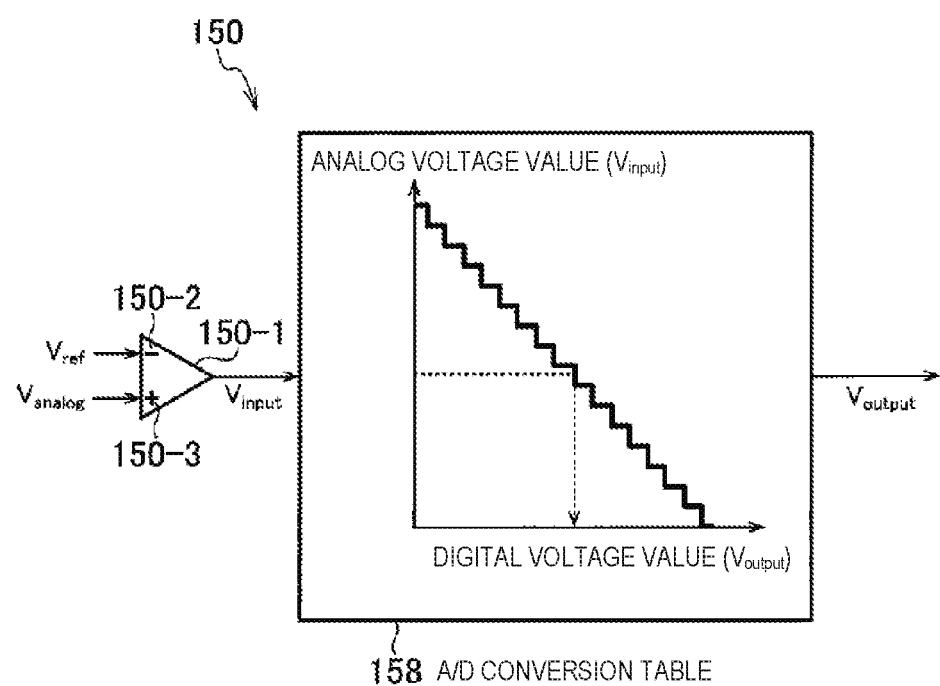
FIG. 18 is a diagram illustrating a block of a voltage sensor according to another example.

FIG. 18 is a diagram illustrating a block of a voltage sensor 150 according to another example. The configuration of the voltage sensor 150 is the same as that illustrated in FIG. 14 except for the voltages to be input to an inverting input terminal 150-2 and a non-inverting input terminal 150-3, and the predetermined correlation (conversion table) 158.

In the present example, the conversion table 158 shows the correlation when the reference voltage ($V_{ref}$) 156 described later is lower than the voltage of the power supply 10, for example, the discharge termination voltage of the power supply 10. In this case, in the predetermined correlation 158, a lower analog voltage value is associated with a higher digital voltage value.

In a general A/D converter using an operational amplifier, the digital value of the value input to the non-inverting input terminal corresponds to the maximum digital value that can be output. In the example illustrated in FIG. 14, since the constant reference voltage ($V_{ref}$) 156 is input to the non-inverting input terminal 150-3, the maximum digital value that can be output is constant. On the other hand, in the example illustrated in FIG. 18, the voltage (analog voltage ($V_{analog}$)) of the power supply 10 that varies according to the charged amount of the power supply 10 can be input to the non-inverting input terminal 150-3. Therefore, the maximum digital value that can be output is variable. Also, the analog value corresponding to the maximum digital value is determined from the calculation capability of the control unit 50 or the voltage sensor 150, regardless of the maximum digital value.

That is, in the example illustrated in FIG. 14, the analog voltage value ($V_{input}$) is converted in the digital value of the voltage of the power supply 10 input to the inverting input terminal 150-2, and is output as the digital output value ($V_{output}$). Furthermore, in the example illustrated in FIG. 18, the analog voltage value ($V_{input}$) is converted in the digital value of the power supply of the power supply 10 input to the non-inverting input terminal 150-3, and is output as the digital output value ($V_{output}$).

Therefore, in the example illustrated in FIG. 14, first, the conversion table 158 is derived from the constant maximum digital value and the constant analog value corresponding thereto. Next, the analog voltage value ($V_{input}$) input to the conversion table 158 is converted into a digital voltage value ($V_{output}$) corresponding thereto, and is output. This digital voltage value ($V_{output}$) corresponds to the digital value of the voltage of the power supply 10 input to the inverting input terminal 150-2.

On the other hand, in the example illustrated in FIG. 18, first, the conversion table 158 is derived from the constant digital value and the analog voltage value ($V_{input}$) corresponding thereto. Next, the conversion table 158 is used to convert a constant analog value corresponding to the maximum digital value to a digital voltage value ($V_{output}$) and the digital voltage value ($V_{output}$) is output. The digital voltage value ($V_{output}$) corresponds to the digital value of the voltage of the power supply 10 input to the non-inverting input terminal 150-3.

Specifically, coordinates of measured or known digital values and analog values corresponding thereto, and the relationship between a predetermined digital voltage value ($V_{output}$) and an analog voltage value ($V_{input}$) may be set as the conversion table 158. As an example, when the relationship between the digital voltage value ($V_{output}$) and the analog voltage value ($V_{input}$) approximates a straight line passing through a predetermined intercept, the conversion table 158 may be set so that the coordinates and the intercept are positioned on the approximate straight line. Note that it will be apparent to those skilled in the art that the relationship between the digital voltage value ($V_{output}$) and the analog voltage value ($V_{input}$) can be approximated not only by a straight line but also by a curve.

In both of the examples illustrated in FIG. 14 and FIG. 18, the measured or known digital values and the analog values corresponding thereto are the digital values of the reference voltage ($V_{ref}$) 156 and the analog values corresponding thereto. In the example illustrated in FIG. 14, since the reference voltage ($V_{ref}$) 156 is input to the non-inverting input terminal 150-3, it is not necessary to measure an analog value corresponding to the reference voltage ($V_{ref}$) 156. On the other hand, in the example illustrated in FIG. 18, it should be noted that since the reference voltage ($V_{ref}$) 156 is input to the inverting input terminal 150-2, it is necessary to measure an analog value corresponding to the reference voltage ($V_{ref}$) 156.

Note that as in the example illustrated in FIG. 14, the analog voltage value ($V_{input}$) is converted into a digital value of the value input to the inverting input terminal 150-2 of the operational amplifier 150-1, and it is known that a larger analog voltage value is associated with a larger digital voltage value in the form output as the digital voltage value ($V_{output}$). On the other hand, as in the example illustrated in FIG. 18, the analog voltage value ($V_{input}$) is converted into a digital value of the value input to the non-inverting input terminal 150-3 of the operational amplifier 150-1, and it should be noted that a smaller analog voltage value is associated with a larger digital voltage value in the form output as the digital voltage value ($V_{output}$).

Here, it is preferable that the predetermined correlation (conversion table) 158 is set so that when the voltage (analog voltage ($V_{analog}$)) of the power supply 10 is a fully charged voltage, the digital voltage value ($V_{output}$) corresponding to the fully charged voltage is output, and when the voltage (analog voltage ($V_{analog}$)) of the power supply 10 is a discharge termination voltage, the digital voltage value ($V_{output}$) corresponding to the discharge terminal voltage is output.

However, an error may be generated in the output digital voltage value ($V_{output}$) due to a product error, degradation of the power supply 10 or the like. Therefore, it is preferable to properly calibrate the predetermined correlation (conversion table) 158 of the voltage sensor 150.

Control regarding calibration of the predetermined correlation (conversion table) 158 can be performed in the same manner as the above-described flowchart (see FIG. 15). As described above, it should be noted that the calibration of the predetermined correlation (conversion table) 158 may be performed by the gain correction shown in FIG. 16 or the offset correction shown in FIG. 17, but in either case, the analog value corresponding to the maximum digital value is calibrated.

However, it is preferable that the predetermined correlation 158 at the time of manufacture or actuation of the inhalation component generation device 100 is calibrated or set so that the analog voltage value ($V_{input}$) higher than the analog voltage value corresponding to the fully charged voltage value when the voltage sensor 150 has no error corresponds to the fully charged voltage value. That is, at the time of manufacture or activation of the inhalation component generation device 100, the voltage sensor 150 is designed to output a digital voltage value corresponding to the fully charged voltage when an analog voltage value associated with the predetermined voltage of the power supply 10 smaller than the fully charged voltage is input to the voltage sensor 150. For example, at the time of manufacture or activation of the inhalation component generation device 100, the voltage sensor 150 may be designed to output a digital voltage value (4.2 V) corresponding to the fully charged voltage when an analog voltage value of 4.1 V smaller than the fully charged voltage (4.2 V) is input to the voltage sensor 150. Thereby, even if there is a manufacturing error, the voltage sensor 150 is configured to output a digital voltage value that is equal to or higher than an actual analog voltage value at the time of manufacture or actuation of the inhalation component generation device 100.

(Voltage of Power Supply Acquired by Control Unit)

The control unit 50 (controller 51) may acquire a digital voltage value ($V_{output}$) output from the voltage sensor 150 when acquiring the voltage of the power supply 10 in all the processes described above. That is, it is preferable that the control unit 50 (controller 51) performs the various types of control described above based on the digital voltage value output from the voltage sensor 150 using the calibrated predetermined correlation 158. As a result, the control unit 50 (controller 51) can accurately perform the various types of control described above.

For example, the power control unit described above may control the power supply from the power supply 10 to the load 121R based on the digital voltage value output from the voltage sensor 150. More specifically, the power control unit may perform the PWM control of the electric power supplied from the power supply 10 to the load 121R based on the digital voltage value.

Also, in another example, the control unit 50 may estimate or detect at least one of degradation and failure of the power supply 10 based on the digital voltage value output from the voltage sensor 150 using the calibrated correlation 158 (first diagnostic function and/or second diagnostic function)

(Program and Storage Medium)

The aforementioned flow illustrated in FIG. 7, FIG. 9, FIG. 12 and FIG. 15 can be performed by the control unit 50. That is, the control unit 50 may have a program that causes the inhalation component generation device 100 to execute the above-described method, and a storage medium in which the program is stored. Furthermore, the aforementioned flow illustrated in FIG. 11 and optionally in FIG. 12 can be performed by the processor 250 of the external charger 200. That is, the processor 250 may have a program that causes a system including the inhalation component generation device 100 and the charger 200 to execute the above-described method, and a storage medium in which the program is stored.

Other Embodiments

Although the present invention has been described by the embodiments described above, it should not be understood that the descriptions and the drawings that form a part of this disclosure limit the present invention. Various alternative embodiments, examples and operation techniques will be apparent to those skilled in the art from this disclosure.

For example, in the first diagnostic function illustrated in FIG. 9, the control unit 50 is configured to estimate or detect at least one of degradation and failure of the power supply 10 based on the value related to the operation amount of the load 121R operated in a period in which the acquired voltage value of the power supply 10 is in a predetermined voltage range. Instead of this, the control unit 50 may configured to be capable of estimating or detecting at least one of degradation and failure of the power supply 10 based on the voltage of the power supply 10 changed in a period in which the acquired value related to the operation amount of the load 121R is in a predetermined range. Even in this case, it should be noted that the degradation or failure of the power supply 10 can be estimated or detected, as described in the above embodiment. Similarly, a method including the steps of acquiring a value related to the operation amount of the load 121R, and estimating or detecting at least one of degradation and failure of the power supply 10 based on the voltage of the power supply 10 changed in a period in which the acquired value related to the operation amount of the load 121R is in a predetermined range is also included in the scope of the present invention. Furthermore, it should be noted that a program for causing the inhalation component generation device 100 to execute such a method is also included in the scope of the present invention.

The invention claimed is:

1. An inhalation component generation device, comprising:
a load configured to vaporize or atomize an inhalation component source with electric power from a power supply; and
circuitry configured to
acquire a value related to an operation amount of the load and a voltage value of the power supply; and
estimate or detect at least one of degradation and failure of the power supply based on the value related to the operation amount of the load operated in a period in which the acquired voltage value of the power supply is in a predetermined voltage range, wherein
the predetermined voltage range is set to a range excluding a plateau range in which a change in voltage value of the power supply with respect to a change in the charged amount of the power supply is smaller than other voltage ranges.

2. An inhalation component generation device, comprising:
a load configured to vaporize or atomize an inhalation component source with electric power from a power supply; and
circuitry configured to
acquire a value related to an operation amount of the load and a voltage value of the power supply;
compare the value related to the operation amount of the load operated in a period in which the acquired voltage value of the power supply is in a predetermined voltage range with a predetermined threshold; and
determine that the power supply has been degraded or has failed in a case that the value related to the operation amount of the load is equal to or less than the predetermined threshold.

3. The inhalation component generation device of claim 2, further comprising:

a sensor configured to output a signal requesting an operation of the load, wherein
the circuitry is configured to derive the value related to the operation amount of the load based on an output of the sensor.

4. The inhalation component generation device of claim 3, further comprising:
an inhalation port for inhaling by a user, wherein
the sensor is configured to output an output a signal that varies depending on inhalation from the inhalation port,
the circuitry is configured to
detect the inhalation based on the signal output by the sensor; and
derive the value related to the operation amount of the load based on at least one of a period or an amount of the detected inhalation.

5. The inhalation component generation device of claim 2, wherein
the circuitry is configured not to perform determination of degradation or failure of the power supply in the predetermined voltage range in a case that a range contributing to vaporization or atomization of the inhalation component source in the predetermined voltage range is equal to or less than a predetermined ratio or width.

6. The inhalation component generation device of the claim 2, wherein
the circuitry is configured to correct to reduce at least one of the predetermined threshold and a lower limit value of the predetermined voltage range in a case that a range contributing to the vaporization or atomization of the inhalation component source in the predetermined voltage range is equal to or less than a predetermined ratio or width.

7. The inhalation component generation device of claim 2, wherein the circuitry is configured to
perform the comparison in each of a plurality of predetermined voltage ranges; and
determine that the power supply has been degraded or has failed in a case that the value related to the operation amount of the load is equal to or less than the predetermined threshold in at least one of the plurality of predetermined voltage ranges.

8. The inhalation component generation device of the claim 7, wherein
the circuitry is configured to estimate or detect at least one of degradation and failure of the power supply based on the value related to the operation amount of the load operated in a period in which the acquired voltage value of the power supply is in a specific voltage range even in the specific voltage range covering one or more of the plurality of predetermined voltage ranges.

9. The inhalation component generation device of claim 8, wherein
the circuitry is configured to not perform determination of degradation or failure of the power supply in an irregular range in which a range contributing to the vaporization or atomization of the inhalation component source among the plurality of predetermined voltage ranges is equal to or less than a predetermined ratio or width, and to exclude the irregular range from the specific voltage range.

10. The inhalation component generation device of claim 8, wherein the circuitry is configured to:
compare the value related to the operation amount of the load operated in a period in which the acquired voltage value of the power supply is in a specific voltage range with a specific threshold even in the specific voltage range covering two or more voltage ranges adjacent to each other among the plurality of predetermined voltage ranges; and determine that the power supply has been degraded or has failed in a case that the value related to the operation amount of the load is equal to or less than the specific threshold, wherein the specific threshold is set to be smaller than a total sum of the predetermined thresholds for comparing the operation amounts of the load in the respective two or more voltage ranges.

11. The inhalation component generation device of claim 10, wherein the circuitry is configured to:

not perform determination of degradation or failure of the power supply in an irregular range in which the range contributing to the vaporization or atomization of the inhalation component source among the plurality of predetermined voltage ranges is equal to or less than a predetermined ratio or width; and exclude the irregular range from the specific voltage range and to subtract, from the specific threshold, a value equal to or less than the predetermined threshold to be compared with the operation amount of the load in the irregular range.

12. The inhalation component generation device of claim 10, wherein the circuitry is configured to, in a case that there is an irregular range in which a range contributing to the vaporization or atomization of the inhalation component source among the plurality of predetermined voltage ranges is equal to or less than a predetermined ratio or width, reduce a predetermined threshold to be compared with the operation amount of the load the an irregular range and the specific threshold.

13. The inhalation component generation device of claim 12, wherein the circuitry is configured to:

acquire a voltage of the power supply while the load is not operating; and correct the predetermined threshold when the voltage of the power supply falls below an upper limit value of the predetermined range without contributing to the vaporization or atomization of the inhalation component source.

14. The inhalation component generation device of claim 7, wherein the plurality of predetermined voltage ranges are set to be narrower as the voltage range in which a change in a voltage value of the power supply with respect to the change in a charged amount of the power supply is smaller.

15. The inhalation component generation device of claim 2, wherein the circuitry is configured to:

integrate, as an integral value, a time in which the voltage of the power supply has dropped without contributing to the vaporization or atomization of the inhalation component source in the predetermined range; and add a value obtained by correcting the integral value based on a predetermined relationship to the value related to the operation amount of the load.

16. The inhalation component generation device of claim 2, wherein the predetermined voltage range is set to a range excluding a plateau range in which a change in voltage value of the power supply with respect to a change in the charged amount of the power supply is smaller than other voltage ranges.

17. The inhalation component generation device of claim 16, wherein the plateau range is defined by a range including both of a plateau range in which, in a new state, a change in the voltage value of the power supply with respect to a change in the charged amount of the power supply is smaller than other voltage ranges and a plateau range in which, in a degraded state, a change in the voltage value of the power supply with respect to a change in the charged amount of the power supply is smaller than other voltage ranges.

18. A method performed by an inhaler device, the method comprising:

acquiring a value related to an operation amount of a load configured to vaporize or atomize an inhalation component source with electric power from a power supply and a voltage value of the power supply;

acquiring a voltage value of the power supply;

comparing the value related to the operation amount of the load operated in a period in which the acquired voltage value of the power supply is in a predetermined voltage range with a predetermined threshold; and determining that the power supply has been degraded or has failed in a case that the value related to the operation amount of the load is equal to or less than the predetermined threshold.

* * * * *